United States Patent
Kraig et al.

(10) Patent No.: US 10,391,150 B2
(45) Date of Patent: *Aug. 27, 2019

(54) TREATMENTS FOR MIGRAINE AND RELATED DISORDERS

(71) Applicant: The University of Chicago, Chicago, IL (US)

(72) Inventors: Richard Kraig, Chicago, IL (US); Aya Pusic, Chicago, IL (US); Heidi Mitchell, Dubuque, IA (US); Yelena Grinberg, Riverside, CA (US); Marcia Kraig, Chicago, IL (US)

(73) Assignee: The Universit of Chicago, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/791,802

(22) Filed: Oct. 24, 2017

(65) Prior Publication Data

US 2018/0036380 A1 Feb. 8, 2018

Related U.S. Application Data

(63) Continuation of application No. 15/171,327, filed on Jun. 2, 2016, now Pat. No. 9,827,294, which is a continuation of application No. 14/234,276, filed as application No. PCT/US2012/047683 on Jul. 20, 2012, now Pat. No. 9,399,053.

(60) Provisional application No. 61/510,673, filed on Jul. 22, 2011.

(51) Int. Cl.
| | |
|---|---|
| *A61K 9/00* | (2006.01) |
| *A61K 31/00* | (2006.01) |
| *A61K 38/18* | (2006.01) |
| *A61K 38/20* | (2006.01) |
| *A61K 38/21* | (2006.01) |
| *A61K 38/28* | (2006.01) |
| *A61K 38/30* | (2006.01) |
| *A61K 45/06* | (2006.01) |

(52) U.S. Cl.
CPC .......... *A61K 38/217* (2013.01); *A61K 9/0043* (2013.01); *A61K 31/00* (2013.01); *A61K 38/18* (2013.01); *A61K 38/2073* (2013.01); *A61K 38/28* (2013.01); *A61K 38/30* (2013.01); *A61K 45/06* (2013.01); *A61K 9/0014* (2013.01)

(58) Field of Classification Search
None
See application file for complete search history.

(56) References Cited

U.S. PATENT DOCUMENTS

| | | | |
|---|---|---|---|
| 2009/0093409 A1 | 4/2009 | Digicaylioglu et al. | |
| 2009/0099077 A1* | 4/2009 | Sur | A61K 38/30 514/20.1 |
| 2009/0238886 A1 | 9/2009 | O'Mahony | |

OTHER PUBLICATIONS

Healthline "the link between chronic migraine and depression" accessed from healthline.com (Year: 2017).*
Akpan et al., "Intranasal delivery of caspase-9 inhibitor reduces caspase-6-dependent axon/neuron loss and improves neurological function after stroke", J. Neurosci., 31(24):8894-8904, 2011.
Aurora, "Spectrum of illness: understanding biological patterns and relationships in chronic migraine", Neurology, 72(5 Suppl):S8-S13, 2009.
Beattie et al., "Control of synaptic strength by glial TNFalpha", Science, 295(5563):2282-2285, 2002.
Belanger et al., "Brain energy metabolism: focus on astrocyte-neuron metabolic cooperation", Cell Metab., 14(6):724-738, 2011.
Benedict et al., "Intranasal insulin improves memory in humans", Psychoneuroendocrinology, 29(10):1326-1334,2004.
Berg, Random Walks in Bilogy, Princeton Univ. Press, NY, 1993.
Born et al., "Sniffing neuropeptides: a transnasal approach to the human brain", Nat. Neurosci., 5(6):514-516, 2002.
Brazier, "The problem of periodicity in the electro-encephalogram: studies in the cat", Electroencephalogr. Clin. Neurophysiol., 15:287-298, 1963.
Buzzi et al., "The antimigraine drug, sumatriptan (GR43175), selectively blocks neurogenic plasma extravasation from blood vessels in dura mater", Br. J. Pharmacol., 99:202-206, 1990.
Cabrera and Milton, "Human stick balancing: tuning Lèvy flights to improve balance control", Chaaos, 14(3):691-698, 2004.
Caggiano et al., "Long-term elevation of cyclooxygenase-2, but not lipoxygenase, in regions synaptically distant from spreading depression", J. Comp. Neurol, 376(3):447-462, 1996.
Carro et al., "Circulating insulin-like growth factor I mediates effects of exercise on the brain", J. Neurosci., 20(8):2926-2933, 2000.
Chen et al., "Pretreatment with interferon-gamma protects microglia from oxidative stress via up-regulation of Mn-SOD", Free Radic Biol. Med., 46(8):1204-1210, 2009.
Clark et al., "Impaired recognition memory in rats after damage to the hippocampus", J. Neurosci., 20(23):8853-8860, 2000.
Correa et al., "The Nrf2-inducible antioxidant defense in astrocytes can be both up- and down-regulated by activated microglia:Involvement of p38 MAPK", Glia, 59(5):785-799, 2011.
Costa-Mattioli et al., "eIF2alpha phosphorylation bidirectionally regulates the switch from short- to long-term synaptic plasticity and memory", Cell, 129(1):195-206, 2007.
Costa-Mattioli et al., "Translational control of hippocampal synaptic plasticity and memory by the eIF2alpha kinase GCN2", Nature, 436(7054):1166-1173, 2005.
Costa-Mattioli et al., "Translational control of long-lasting synaptic plasticity and memory", Neuron., 61(1):10-26, 2009.

(Continued)

*Primary Examiner* — Adam Weidner
(74) *Attorney, Agent, or Firm* — Norton Rose Fulbright US LLP

(57) ABSTRACT

Embodiments are directed to compositions and methods of treating migraine and related neurological disorders. In certain aspects, methods and compositions are for reducing cortical spreading depression and/or suppressing the neurochemical basis for chronic and acute migraine events, and provide methods and pharmaceutical compositions related to both acute and preventive therapies for migraine events and related headaches.

5 Claims, 15 Drawing Sheets

Specification includes a Sequence Listing.

(56) References Cited

OTHER PUBLICATIONS

Darabaneanu et al., "Aerobic exercise as a therapy option for migraine: a pilot study", Int. J. Sports Med., 32(6):455-460, 2011.
De Rosa et al., "Intranasal administration of nerve growth factor (NGF) rescues recognition memory deficits in AD11 anti-NGF transgenic mice", Proc. Natl. Acad. Sci. USA., 102(10):3811-3816, 2005.
Empl et al., "T-cell subsets and expression of integrins in peripheral blood of patients with migraine", Cephalalgia, 19(8):713-717, 1999.
Engelhardt and Ransohoff, "The ins and outs of T-lymphocyte trafficking to the CNS: anatomical sites and molecular mechanisms", Trends Immunol., 26(9):485-495, 2005.
Gkogkas et al., "Translational control mechanisms in long-lasting synaptic plasticity and memory", J. Biol. Chem., 285(42):31913-31917, 2010.
Gobbo and O'Mara, "Impact of enriched-environment housing on brain-derived neurotrophic factor and on cognitive performance after a transient global ischemia", Behav. Brain Res., 152(2):231-241, 2004.
Goddard et al., "Regulation of CNS synapses by neuronal MHC class I", Proc. Natl. Acad. Sci. USA., 104(16):6828-6833, 2007.
Grinberg and Kraig, "Oxidative stress from spreading depression preferentially rises in astrocytes and microglia, with the latter effect mitigated by IGF-1", Soc. Neurosci., 38:(In Press), 2012b.
Grinberg et al., "Insulin-like growth factor-1 lowers spreading depression susceptibility and reduces oxidative stress", J. Neurochem., 122(1):221-229, 2012.
Guedes et al., "Malnutrition and brain function: experimental studies using the phenomenon of cortical spreading depression", Rev. Bras Biol., 56(Su 1 Pt. 2):293-301, 1996.
Gulati et al., "Possible role of free radicals in theophylline-induced seizures in mice", Pharmacology, Biochemistry and Behavior, 82:241-245, 2005.
Hallschmid et al., "Towards the therapeutic use of intranasal neuropeptide administration in metabolic and cognitive disordersa", Regul Pept., 149(1-3):79-83, 2008.
Haskew-Layton et al., "Controlled enzymatic production of astrocytic hydrogen peroxide protects neurons from oxidative stress via an Nrf2-independent pathway", Proc. Natl. Acad. Sci. USA, 107(40):17385-17390, 2010.
Hulse et al., "Monomeric IgG is neuroprotective via enhancing microglial recycling endocytosis and TNF-alpha", J. Neurosci., 28(47):12199-12211, 2008.
Hung et al., "The mechanism of heme oxygenase-1 action involved in the enhancement of neurotrophic factor expression", Neuropharmacology, 58(2):321-329, 2010.
Imitola et al., "Cytokines in multiple sclerosis: from bench to bedside", Pharmacol. Ther., 106(2):163-177, 2005.
International Search Report and Written Opinion issued in PCT/US2012/04683, dated Jan. 23, 2013.
Jogie-Brahim et al., "Unraveling insulin-like growth factor binding protein-3 actions in human disease", Endocr. Rev., 30(5):417-437, 2009.
Juliana, "Anti-inflammatory compounds parthenolide and Bay 11-7082 are direct inhibitors of the inflammasome", *J Biol Chem*, 285:9792-9802, 2010.
Jurrlink et al., "Peroxide-scavenging deficit underlies oligodendrocyte susceptibility to oxidative stress", Glia, 22(4):371-378, 1998.
Kaneko et al., "Characteristics of bone marrow-derived microglia in the normal and injured retina", Invest. Ophthalmol Vis Sci., 49(9):4162-4168, 2008.
Kishida and Klann, "Sources and targets of reactive oxygen species in synaptic plasticity and memory", Antioxid. Redox. Signal, 9(2):233-244, 2007.
Koekkoek et al., "Intensive multifactorial treatment and cognitive functioning in screen-detected type 2 diabetes—The Addition—Netherlands study: A cluster-randomized trial", Journal of Neurological Sciences, 314:71-77, 2012.
Kopec et al., "Glutamate receptor exocytosis and spine enlargement during chemically induced long-term potentiation", J. Neurosci., 26(7):2000-2009, 2006.
Kraig et al., "TNF-α and Microglial Hormetic Involvement in Neurological Health & Migraine", Dose Response, 8(4):389-413, 2010.
Kruger et al., "Repetitive spreading depression causes selective suppression of GABAergic function", Neuroreport, 7(15-17):2733-2736, 1996.
Kunkler and Kraig, "Calcium waves precede electrophysiological changes of spreading depression in hippocampal organ cultures", J. Neurosci., 18(9):3416-3425, 1998.
Kunkler and Kraig, "Hippocampal spreading depression bilaterally activates the caudal trigeminal nucleus in rodents", Hippocampus, 13(7):835-844, 2003.
Kunkler and Kraig, "Reactive astrocytosis from excitotoxic injury in hippocampal organ culture parallels that seen in vivo", J. Cereb. Blood Flow Metab., 17(1):26-43, 1997.
Kunkler et al., "Multiplexed cytokine protein expression profiles from spreading depression in hippocampal organotypic cultures", J. Cereb. Blood Flow Metab., 24(8):829-839, 2004.
Kunkler et al., "Neural activity-dependent modulation of myelination", Sco. Neurosi., 32:87.5, 2006.
Kunkler et al., "Optical current source density analysis in hippocampal organotypic culture shows that spreading depression occurs with uniquely reversing currents", J. Neurosci., 25(15):3952-3961, 2005.
Lamas et al., "Effects of Interferon-gamma on Nitric Oxide Synthase Activity and Endothelin-1 Production by Vascular Endothelial Cells", J. Clin. Nvest, 90:879-887, 1992.
Lauritzen and Kraig, "Spreading Depression", In:The Headaches,Olsen et al. (Eds), 3rd Ed., Lippincott-Raven, Philadelphia, p. 269-276, 2005.
Lees and Cross, "A little stress is good: IFN-gamma, demyelination, and multiple sclerosis", J. Clin. Invest., 117(2):297-299, 2007.
Li et al., "Regional distribution of cortical interneurons and development of inhibitory tone are regulated by Cxcl12/Cxcr4 signaling", J. Neurosci., 28(5):1085-1098, 2008.
Lin et al., "Enhanced integrated stress response promotes myelinating oligodendrocyte survival in response to interferon-gamma", Am. J. Pathol., 173(5):1508-1517, 2008.
Lovatt et al., "The transcriptome and metabolic gene signature of protoplasmic astrocytes in the adult murine cortex", J. Nerosci., 27(45):12255-12266, 2007.
Mansuy et al., "Restricted and regulated overexpression reveals calcineurin as a key component in the transition from short-term to long-term memory", Cell., 92(1):39-49, 1998.
Mariani, "Targeting Cancer Cells—More pathways, more inhibitors, more trials" Highlights of 9th annual drug discovery technology world congress; Boston, MA. Accessed from www.medscape.com.
McGlade-McCulloh et al., "Individual microglia move rapidly and directly to nerve lesions in the leech central nervous system", Proc. Natl. Acad. Sci. USA, 86(3):1093-1097, 1989.
MedlinePlus 2015 "Migraine" accessed from www.nlm.nih.gov/medlineplus.
Mendes et al., "Lithium reduces Gsk3b mRNA levels: implications for Alzheimer Disease", Eur. Arch Psychiatry Clin. Neurosci., 259(1):16-22, 2009.
Merkler et al., "Propagation of spreading depression inversely correlates with cortical myelin content", Ann. Neurol., 66(3):355-365, 2009.
Mitchell et al., "Cold pre-conditioning neuroprotection depends on TNF-α and is enhanced by blockade of interleukin-11", J. Neurochem., 117(2):187-196, 2011.
Mitchell et al., "Strategies for study of neuroprotection from cold-preconditioning", J. Vis. Exp., 2(43):pii02192, 2010.
Mody et al., "Low extracellular magnesium induces epileptiform activity and spreading depression in rat hippocampal slices", J. Neurophysiol., 57(3):869-888, 1987.
Muller et al., "Effects of interferons and hydrogen peroxide on CA3 pyramidal cells in rat hippocampal slice cultures", Brain Research, 619:157-162, 1993.

(56) References Cited

OTHER PUBLICATIONS

Mumby et al., "Hippocampal damage and exploratory preferences in rats: memory for objects, places, and contexts", Learn Mem., 9(2):49-57, 2002.
Nimmerjahn et al., "Resting microglial cells are highly dynamic surveillants of brain parenchyma in vivo", Science, 308(5726):1314-1318, 2005.
Nishijima et al., "Neuronal activity drives localized blood-brain-barrier transport of serum insulin-like growth factor-I into the CNS", Neuron, 67(5):834-846, 2010.
Nunez et al., "Insulin-like growth factor I modifies electrophysiological properties of rat brain stem neurons", J. Neurophysiol., 89(6):3008-3017, 2003.
O'Brien et al., "Laminin α2(merosine)-deficient muscular dystrophy and demyelinating neuropathy in two cats", Journal of the Neurological Science, 189:37-43, 2001.
Otamkhov et al., "Forskolin-induced LTP in the CA1 hippocampal region is NMDA receptor dependent", J. Neurophysiol., 91(5):1955-1962, 2004.
Otamkhov et al., "Persistent accumulation of calcium/calmodulin-dependent protein kinase II in dendritic spines after induction of NMDA receptor-dependent chemical long-term potentiation", J. Neurosci., 24(42):9324-9331, 2004.
Papadia et al., "Synaptic NMDA receptor activity boosts intrinsic antioxidant defenses", Nat. Neurosci., 11(4):476-487, 2008.
Popko et al., "The effects of interferon-gamma on the central nervous system", Mol. Neurobiol., 14(1-2):19-35, 1997.
Pusic and Kraig, "Inflammatory gene micro array profiling demonstrates 'T-cell-like' activation after recurrent spreading depression—Implications for migraine pathogenesis", Soc. Neurosci., 36:Prog #346.2, 2010.
Pusic et al., "Modeling neural immune signaling of episodic and chronic migraine using spreading depression in vitro", J. Vis. Exp., 52:2910, 2011.
Ramirez et al., "Inhibition of glycogen synthase kinase 3beta (GSK3beta) decreases inflammatory responses in brain endothelial cells", Am. J. Pathol., 176(2):881-892, 2010.
Rampon et al., "Enrichment induces structural changes and recovery from nonspatial memory deficits in CA1 NMDAR1-knockout mice", Nat. Neurosci., 3(3):238-244, 2000.
Ramsey et al., "Functional characterization of des-IGF-1 action at excitatory synapses in the CA1 region of rat hippocampus", J. Neurophysiol., 94(1):247-254, 2005.
Ren et al., "Brusatol enhances the efficacy of chemotherapy by inhibiting the Nrf2-mediated defense mechanism", Proc. Natl. Acad. Sci. USA, 108(4):1433-1438, 2011.
Reuter et al., "Nuclear Factor-kB as a Molecular Target for Migraine Therapy", Ann. Neurol., 51:507-516, 2002.
Reynolds, "Animals that randomly reorient at cues left by correlated random walkers do the Lévy walk", Am. Nat., 175(5):607-613, 2010b.
Reynolds, "Bridging the gulf between correlated random walks and Lévy walks: autocorrelation as a source of Lévy walk movement patterns", J. R. Soc. Interface, 7(53):1753-1758, 2010.
Rohl et al., "Activated microglia modulate astroglial enzymes involved in oxidative and inflammatory stress and increase the resistance of astrocytes to oxidative stress in vitro", Glia, 56(10):1114-1126, 2008.
Romera et al., "In vitro ischemic tolerance involves upregulation of glutamate transport partly mediated by the TACE/ADAM17-tumor necrosis factor-alpha pathway", J. Neurosci., 24(6):1350-1357, 2004.
Ruby et al., "Hippocampal-dependent learning requires a functional circadian system", Proc. Natl. Acad. Sci. USA, 105(40):15593-15598, 2008.
Selmeczi et al., "Cell motility as persistent random motion: theories from experiments", Biophys J., 89(2):912-931, 2005.
Selmeczi et al., "Cell motility as random motion: A review", In: The European Physical Journal Special Topics, 157(1):1-5, Springer Berlin/Heidelberg, 2008.
Shao and Dudek, "Both synaptic and intrinsic mechanisms underlie the different properties of population bursts in the hippocampal CA3 area of immature versus adult rats", J. Physiol., 587(Pt 24):5907-5923, 2009.
Silberstein and Olesen, "Cronich Migraines", In: The Headaches, 3rd Ed., Olsen et al. (Eds.), p. 613-617, Philadelphia, Lippincott-Raven, 2005.
Steinmetz and Turrigiano, "Tumor necrosis factor-α signaling maintains the ability of cortical synapses to express synaptic scaling", J. Neurosci., 30(44):14685-14690, 2010.
Stellwagen and Malenka, "Synaptic scaling mediated by glial TNF-alpha", Nature, 440(7087):1054-1059, 2006.
Stellwagen et al., "Differential regulation of AMPA receptor and GABA receptor trafficking by tumor necrosis factor-alpha", J. Neurosci., 25(12):3219-3228, 2005.
Stockhorst et al., "Insulin and the CNS: effects on food intake, memory, and endocrine parameters and the role of intranasal insulin administration in humans", Physiol. Behave., 83(1):47-54, 2004.
Takagi et al., "Functional analysis of spontaneous cell movement under different physiological conditions", PLoS One, 3(7):e2648, 2008.
Thorne et al., "Delivery of insulin-like growth factor-I to the rat brain and spinal cord along olfactory and trigeminal pathways following intranasal administration", Neuroscience, 127(2):481-496, 2004.
Thuret et al., "Hippocampus-dependent learning is associated with adult neurogenesis in MRL/MpJ mice", Hippocampus, 19(7):658-669, 2009.
Trepicchio et al., "Recombinant Human IL-11 Attenuates the Inflammatory Response Cytokine Through Down-Regulation of Proinflammatory Release and Nitric Oxide Production", J. Immunol, 157:3627-3634, 1996.
Viswanathan et al., "Optimizing the success of random searches", Nature, 401(6756):911-914, 1999.
Waldbaum and Dudek, "Single and repetitive paired-pulse suppression: a parametric analysis and assessment of usefulness in epilepsy research", Epilepsia, 50(4):904-916, 2009.
Waldbaum and Patel, "Mitochondria, oxidative stress, and temporal lobe epilepsy", Epilepsy Res., 88(1):23-45, 2010.
Young et al., "Environmental enrichment inhibits spontaneous apoptosis, prevents seizures and is neuroprotective", Nat. Med., 5(4):448-453, 1999.
Ziv et al., "Immune cells contribute to the maintenance of neurogenesis and spatial learning abilities in adulthood.", Nat. Neurosci., 9(2):268-275, 2006.

* cited by examiner

TREATMENTS FOR MIGRAINE AND RELATED DISORDERS

CROSS-REFERENCE TO RELATED APPLICATIONS

This application is a continuation of U.S. patent application Ser. No. 15/171,327 filed Jun. 2, 2016, which is a continuation of U.S. patent application Ser. No. 14/234,276 filed Jan. 22, 2014, which is a national phase application under 35 U.S.C. § 371 of International Application No. PCT/US2012/047683 filed Jul. 20, 2012, which claims priority to U.S. Application No. 61/510,673 filed on Jul. 22, 2011. The entire contents of each of the above-referenced disclosures are specifically incorporated herein by reference without disclaimer.

STATEMENT OF FEDERAL FUNDING

This invention was made with government support under Contract No. NS019108 awarded by the National Institute of Neurological Disorders and Stroke of the National Institutes of Health. The government has certain rights in the invention.

FIELD OF THE INVENTION

The present invention relates generally to medicine and neurology. In particular, embodiments are directed to the treatment of migraine and related neurological disorders.

BACKGROUND OF THE INVENTION

Migraine headache is a complex, recurrent disorder that is one of the most common complaints in medicine. In the United States, more than 30 million people have one or more migraine headaches per year. Approximately 75% of all persons who experience migraines are women.

Migraine was previously considered a vascular phenomenon that resulted from intracranial vasoconstriction followed by rebound vasodilation. Currently, however, the neurovascular theory describes migraine as primarily a neurogenic process with secondary changes in cerebral perfusion. The neurovascular theory holds that a complex series of neural and vascular events initiates migraine.

The theory of cortical spreading depression (CSD) has been advanced to explain the neurologic mechanism of migraine with aura. CSD is a well-defined wave of initial neuronal excitation followed by neuronal silence and then again excitation that returns to normal in cortical gray matter areas that spreads from its site of origin. This transient cellular depolarization is understood to cause the primary cortical phenomenon or aura phase; in turn, it activates trigeminal fibers causing the headache phase. Similar changes are understood to cause pain from migraine with and without aura. CSD is a wave of electrophysiological hyperactivity followed by a wave of inhibition, most often noted in the visual cortex. The scintillating scotoma (visual aura) of migraine in humans may be related to the neurophysiologic phenomenon termed the spreading depression of Leão.

Migraine treatment involves acute (abortive) and preventive (prophylactic) therapy. Patients with frequent attacks may require both. Acute treatments are intended to stop or prevent the progression of a headache or reverse a headache that has started. Preventive treatment, which is given even in the absence of a headache, is intended to reduce the frequency and severity of the migraine attack, make acute attacks more responsive to abortive therapy, and perhaps also improve the patient's quality of life. There remains a need for additional therapies for treating migraine or other neurological disorders.

SUMMARY OF THE INVENTION

Methods and compositions are provided based on experimental data showing that they can achieve a desired physiological effect that may be implemented to treat migraine patients—patients who have previously suffered from a migraine and who are at risk for suffering from future migraines. Treatment of a migraine patient will be understood to reduce or limit the frequency, severity, and/or duration of migraines. It is also contemplated that methods and compositions can also be implemented as discussed in embodiments below to effect prevention of migraines. In certain aspects, methods and compositions inhibit spreading depression and migraine events. Such methods and compositions are contemplated in some embodiments for use on a human subject.

In some embodiments, methods are provided for treating a migraine patient comprising administering to the patient interleukin-11 (IL-11) or a composition comprising IL-11. In other embodiments there are methods for treating chronic or recurrent migraines in a patient comprising administering to the patient IL-11 or a composition comprising IL-11.

In some embodiments, methods are provided for treating a migraine patient comprising administering to the patient an insulin-like growth factor receptor (IGFR) inducer or a composition comprising an IGFR inducer. In certain embodiments, the IGFR inducer is IGF-1 or insulin. In specific embodiments, the IGFR inducer is IGF-1. In other embodiments, the IGFR inducer is insulin. In further embodiments there are methods for treating chronic or recurrent migraines in a patient comprising administering to the patient IGF-1 or a composition comprising IGF-1. In additional embodiments, there are methods for treating a migraine patient comprising administering to the patient insulin or a composition comprising insulin. In other embodiments there are methods for treating chronic or recurrent migraines in a patient comprising administering to the patient insulin or a composition comprising insulin. In particular embodiments, there are methods for treating a migraine patient comprising administering to the patient an IGFR inducer or a composition comprising an IGFR inducer, wherein the IGFR inducer is a polypeptide. In other embodiments, the IGFR inducer is not insulin. Moreover, it is specifically contemplated that when insulin is included in some embodiments for treating migraine or a migraine patient that the insulin is not ingested or administered subcutaneously.

Additional aspects include methods for treating a migraine patient comprising administering to the patient interferon-gamma (IFN-γ) or a composition comprising IFN-γ. In other embodiments there are methods for treating chronic or recurrent migraines in a patient comprising administering to the patient IFN-γ or a composition comprising IFN-γ.

In further embodiments there are methods for treating a migraine patient comprising administering to the patient IL-11, IFN-γ, and/or IGF-1. In additional aspects, there are methods for treating a migraine patient comprising administering intranasally to brain cells of the patient an effective amount of a composition comprising IL-11, IFN-γ, IGF-1, and/or insulin. In other embodiments there are methods for treating chronic or recurrent migraines in a patient comprising administering intranasally to the patient an effective amount IL-11, IFN-γ, IGF-1, and/or insulin.

In certain embodiments, the patient is suffering from symptoms of a migraine headache when the composition is administered. A migraine typically includes a unilateral, throbbing moderate to severe headache. Other symptoms of migraines include, but are not limited to, nausea, aura, blurred vision, delirium, nasal stuffiness, diarrhea, tinnitus, polyuria, pallor, sweating, localized edema of the scalp or face, scalp tenderness, prominence of a vein or artery in the temple, stiffness and tenderness of the neck, impairment of concentration and mood, or cold and moist feeling in appendages.

In further embodiments, the patient is a chronic or recurrent migraine patient, which means the patient experiences headaches more than half the time, for 15 days or more in a month, for at least three months. In certain embodiments, the patient has tried one or more acute treatment options such as simple analgesics, non-steroidal anti-inflammatory drugs (NSAIDS), triptans, and ergotamines and has not experienced significant pain relief.

It is contemplated that the patient is administered an amount that is considered effective or has been effective in other patients for achieving a beneficial effect with respect to migraines or symptoms of a migraine. An effective amount of IL-11, IFN-γ, IGF-1 and/or insulin is administered to or by a patient.

The rationale for phasic delivery of the proposed therapeutic agents for migraine begins to be illustrated in FIG. 1B (3-4). In general, this means that patient exposure to the therapeutic agents is not constant. Instead, agents are administered to initiate an adaptive response (3), which is then allowed to develop (4), in the absence of continued agent exposure, before the agent is delivered again. Exemplary evidence supporting the advantage of this approach is provided for IGF-1 using hippocampal slice cultures (FIGS. 5, 8), where for seven days, IGF-1 was administered every 12 hours and removed for successive intervening 12 hours before testing SD susceptibility. This afforded maximal and continued protection against CSD. Also, maximal IFN-γ-based protection against CSD was seen when IFN-γ was pulsed onto slice cultures for only 12 hours once a week (FIGS. 5, 15, 16). In each case this pattern of agent delivery was chosen to mimic phasic effects of environmental enrichment (EE) that consists of exercise-rest-exercise cycles.

In some methods, the composition is administered to the patient intranasally. In certain embodiments the composition is administered to the patient's brain cells or brain tissue. In additional embodiments, the composition is administered to microglia in the patient's brain. It is specifically contemplated that neurons, microglia, oligodendrocytes or astrocytes in the patient's brain are contacted with a composition comprising IL-11, IFN-γ, IGF-1, and/or insulin.

The IL-11, IFN-γ, IGF-1, or insulin is purified and/or isolated in embodiments described herein. These polypeptides may be recombinantly produced or they may be synthetic.

In some embodiments, the composition is a liquid. In other embodiments, the composition is a gel or a powder. It is specifically contemplated that the composition may be a liquid that is provided to the patient as a mist.

Methods may involve administering a composition containing about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nanograms (ng), micrograms (mcg), milligrams (mg), or grams of IL-11, IFN-γ, IGF-1, and/or insulin, or any range derivable therein.

Alternatively, embodiments may involve providing or administering to the patient or to cells or tissue of the patient about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nanograms (ng), micrograms (mcg), milligrams (mg), or grams of IL-11, IFN-γ, IGF-1, and/or insulin, or any range derivable therein, in one dose or collectively in multiple doses. In some embodiments, the composition comprises between about 0.1 ng and about 2.0 g of IL-11, IFN-γ, IGF-1, and/or insulin. The above numerical values may also be the dosage that is administered to the patient based on the patient's weight, expressed as ng/kg, mcg/kg, or mg/kg, and any range derivable from those values.

Alternatively, the composition may have a concentration of IL-11 that is 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 ng/ml, µg/ml, mg/ml, or g/ml, or any range derivable therein.

If a liquid, gel, or semi-solid composition, the volume of the composition that is administered to the patient may be about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 microliters (µl) or milliliters (ml), or any range derivable therein. In certain embodiments, the patient is administered up to about 10 ml of the composition.

The amount of IL-11, IFN-γ, IGF-1, and/or insulin that is administered or taken by the patient may be based on the patient's weight (in kilograms). Therefore, in some embodiments, the patient is administered or takes a dose or multiple doses amounting to about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 µg/kilogram (kg) or mg/kg, or any range derivable therein.

The composition may be administered to (or taken by) the patient 1, 2, 3, 4, 5, 6, 7, 8, 9, 10, 11, 12, 13, 14, 15, 16, 17, 18, 19, 20 or more times, or any range derivable therein, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range derivable therein. It is specifically contemplated that the composition may be administered once daily, twice daily, three times daily, four times daily, five times daily, or six times daily (or any range derivable therein) and/or as needed to the patient. Alternatively, the composition may be administered every 2, 4, 6, 8, 12 or 24 hours (or any range derivable therein) to or by the patient. In some embodiments, the patient is administered the composition for a certain period of time or with a certain number of doses after experiencing symptoms of a migraine. In particular embodiments, IGF-1 may be administered once a day; IFN-γ may be administered once every week.

In particular embodiments, the composition may be administered to the patient in a phases or cycles. For example, the composition may be administered to the patient, wherein the composition is at an amount that the active compound (IL-11, IFN-γ, IGF-1, or insulin) in the composition is no longer bioavailable or therapeutically effective within a first period of time of administration, such as after 1, 2, 3, 4, 5, 6, 7, 8, 9, 10, 11, 12, 13, 14, 15, 16, 17, 18, 19, 20, 21, 22, 23, 24 hours, preferably 12 hours. The composition may be re-administered to the patient after a second period of time from the end of the first period of time, such as after 1, 2, 3, 4, 5, 6, 7, 8, 9, 10, 11, 12, 13, 14, 15, 16, 17, 18, 19, 20, 21, 22, 23, 24 hours, preferably 12 hours. The compound may be IL-11, IFN-γ, IGF-1, or insulin. For example, IFN-γ or IGF-1 may be administered and they may be cleared from the body after 12 hours, but the second dose of IFN-γ or IGF-1 may not be resumed until after another 12 hours-during the second 12 hours the patient does not have the administered IFN-γ or IGF-1.

In some embodiments, methods also include administering to the patient more than one of the following compounds: IL-11, IFN-γ, IGF-1, or insulin. It is contemplated that the combination may be administered to the patient concurrently (at the same time) and in the same composition, concurrently but in separate compositions, or serially.

In certain embodiments, IL-11 and IFN-γ are administered to or taken by the patient. In some embodiments, IL-11 and IGF-1 are administered to or taken by the patient. In additional embodiments, IL-11 and insulin are administered to or taken by the patient. In embodiments involving IL-11, IL-11 may be administered to or by the patient prior to or after the other compound.

In other embodiments, IFN-γ and IGF-1 are administered to or taken by the patient. In some embodiments, IFN-γ and insulin are administered to or taken by the patient. In embodiments involving IFN-γ, IFN-γ may be administered to or by the patient prior to or after the other compound.

In some aspects, IGF-1 and insulin are administered to or taken by the patient. IGF-1 may be administered to or by the patient prior to or after the insulin.

In other embodiments, one or more of IL-11, IFN-γ, IGF-1, or insulin may be administered to or by a patient who is also given or taking an anti-migraine drug. In certain aspects the composition also includes an anti-migraine drug, which may be either a pain-relieving medication or a preventative medication. Pain relieving medications include but are not limited to pain relievers such as NSAIDs or acetaminophen, a combination of acetaminophen, aspirin, and caffeine, triptans, ergotamine and caffeine combination drugs, anti-nausea medication, opiates, such as codeine, and a corticosteroid such as dexamethasone. Preventative medications include but are not limited to beta blockers, antidepressants such as tricyclic antidepressants, an anti-seizure drug, cyproheptadine, or botulinum toxin type A. In some embodiments, the patient is administered the anti-migraine drug within 1, 2, 3, 4, 5, 6, 7, 8, 9, 10, 11, 12, 13, 14, 15, 16, 17, 18, 19, 20, 21, 22, 23, or 24 hours, or any range derivable therein, of being administered the composition containing one or more of IL-11, IFN-γ, IGF-1, and/or insulin.

In some embodiments a polypeptide such as IL-11, IFN-γ, or IGF-1 is not provided directly to the patient or to cells of the patient, and instead, the patient is provided with an expression vector that comprises a nucleic acid sequence encoding the polypeptide under the control of a promoter, wherein the polypeptide is expressed in a cell containing the vector. Consequently, embodiments involving polypeptides may be implemented with an expression vector to achieve a treatment for migraine patients.

Other embodiments are discussed throughout this application. Any embodiment discussed with respect to one aspect applies to other aspects as well and vice versa. The embodiments in the Example section are understood to be embodiments of the invention that are applicable to all aspects of the invention.

The terms "ameliorating," "inhibiting," or "reducing," or any variation of these terms, when used in the claims and/or the specification includes any measurable decrease or complete inhibition to achieve a desired result.

Throughout this application, the term "effective amount" is used to indicate that the compounds are administered at an amount sufficient to treat a condition in a subject in need thereof. In some embodiments, the condition is, but is not limited to, acute or chronic migraine, or other conditions associated with acute or chronic migraine, or conditions associated with cortical spreading depression (CSD).

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) Experiments begin with determination of the current needed to maximize standard CA3 area field potential responses. Half-maximal intensity is then used to elicit CA3 area evoked field potentials from dentate gyrus bipolar electrical stimulation. This documents the normalcy of evoked synaptic responses between preparations. If a slice's field excitatory post synaptic potentials are not at least 3 mV, slices are discarded. Next, field potential trains (i) are noted to verify that preparations are healthy enough to follow 10 Hz stimulation (e.g., amplitudes of vertical deviations in fast potential records are similar) and the current needed to trigger SD (ii) is registered (Pusic and Kraig, 2010). (FIG. 2B) For example, SD threshold is significantly (p<0.001; n=13 & 17, respectively) reduced 3 days after 6 SDs elicited over an hr compared to control. (FIG. 2C) This effect is significantly (p<0.002; n=37 & 10, respectively) related to TNF-α since it can be mimicked by 3 day exposure (100 ng/mL) to TNF-α compared to control. (FIG. 2D) Also, SD threshold is significantly (p<0.001; n=37 & 15, respectively) increased by removal of TNF-α signaling via inclusion of sTNFR1 (100 ng/mL) compared to control. (FIG. 2E) Finally, minocycline (MinoC; 10 μg/mL), which prevents increased production of TNF-α from microglia (Hulse et al., 2008) significantly (p<0.002; n=9 & 3, respectively) increases SD threshold compared to control (Mitchell et al., 2010).

(FIG. 1A) CD-6 (surface marker for T-cells; yellow arrow) positive T-cells within the parenchyma of a mature (>21 days in vitro) hippocampal slice culture maintained in serum-free media. (Pusic et al., 2011). Cal bar, 15 μm. (FIG. 1B) When activated, T-cells in slice cultures are immunopositive for IFN-γ (yellow arrows). Cal bar, 30 μm. (FIG. 1C) Acute (15-60 min) exposure to IFN-γ (500 U/mL) triggers a significant (p<0.001; n=5 for each group) increase in SD susceptibility.

(FIG. 4A) Normal cytoarchitecture of a hippocampal slice culture showing pyramidal neuron areas of CA1, dentate gyrus (DG), and the imaging zone for the inventors' work here (dotted line), CA3. (FIG. 4B) OS was measured using CellROX, a fixable fluorescent marker from Invitrogen. Image shows OS 24 hours after 6 SDs. (FIG. 4C) Pre-incubation in IGF-1 (40 ng/mL for 3 days before SD) triggered a reduction in OS measured a day later. (FIG. 4D) This reduction versus control SD was significant (p<0.02; n=4 & 5). (FIG. 4E) CellROX can be used to measure relative OS in specific brain cell types. Image in FIG. 4A shows a pyramidal neuron from a slice culture labeled with NeuN. (FIG. 4F) Co-labeled image of CellROX shows associated OS.

(FIG. 7A) Nasal injection setup showing heat lamp and thermo-regulator that maintains temperature at 37° C. plus nose cone used to deliver isoflurane anesthesia. (FIG. 7B) Operator is shown administering nasal IGF-1 solution, which is performed in a fume hood to adequately vent isoflurane from nose cone. (FIG. 7C) Image illustrates standard electrophysiology setup. Anesthetized animal is placed into a standard electrophysiology holder and anesthesia maintained by a nose cone delivering 3% isoflurane in oxygen. Arterial oxygen saturation is monitored with a pulse-oximeter. Animals are warmed to 37.5° C. with a heating plate. SD is induced by progressively injecting larger volumes of 0.5 M KCl from an 8 μm diameter microelectrode. SD is registered with a second microelectrode used for DC recordings placed more caudally. After SD is evoked by a given injection pulse, the stimulating electrode is withdrawn and a volume re-injected under mineral oil. The diameter of the resultant KCl injection sphere is then measured off line using a compound microscope and the injection volume calculated. For example, in the above whole animal experiments it took 1-8 nL of 0.5 M KCl to evoke SD in control brain regions while after acute IGF-1 this amount rose to 67-109 nL. A day after IGF-1 treatment the volume needed to evoked SD was 34-48 nL. IFN-γ treatment required 338 nL of 0.5 M KCl a day after treatment and IL-11 required 67-200 nL. On the other hand, while still significantly greater than control, acute insulin treatment only required 8-34 nL.

(FIG. 8a) Exemplary CA3 area evoked field potential. Experiments begin with establishment of the current intensity needed to evoke maximal field potential responses; stimuli of half-maximal intensity were then used to elicit subsequent field potentials. Only those cultures with CA3 pyramidal neuron post-synaptic responses of at least 3 mV were used for experiments. (FIG. 8b) CA3 response to dentate gyrus bipolar stimulation (10 pulses at 10 Hz, 500 μA) was used to elicit a spreading depression (SD), as shown in (FIG. 8c). (FIG. 8c) The spreading depression (SD) shown here was induced by the stimulation/response (arrow) shown in (FIG. 8b). (FIG. 8d) Average current necessary to induce SD (SD threshold) was significantly (*p=0.001) higher when slice cultures were exposed to 40 ng/mL IGF-1 acutely (n=6 and 7 for control and experimental slices, respectively). (FIG. 8e) Similarly, average SD threshold was also significantly (*p<0.001) increased when slice cultures were exposed to IGF-1 for 3 days prior to SD (n=8 and 7 for control and experimental slices, respectively). (FIG. 8f) Finally, average SD threshold was significantly (*p<0.001) increased when slice cultures were exposed to IGF-1 for 7 days prior to SD (n=11 and 6 for control and experimental slices, respectively.) Here the seve-day treatment was phasic—cultures were exposed to IGF-1 for only 12 hours a day for seven days to better mimic phasic effects of exercise-rest-exercise seen with EE. Comparisons between groups made via Student's t-test.

(FIG. 9a) NeuN immunohistochemical labeling of a hippocampal slice culture, for cytoarchitectural reference and to show the CA3 area of interest (dotted line box) used for quantification of oxidative stress (OS) via CellROX™ fluorescence intensity. (FIGS. 9b-c) Representative CellROX™-labeled hippocampal slices exposed to SD (FIG. 9b) and to 3-day IGF-1 incubation followed by spreading depression (SD) (FIG. 9c). Dotted line boxes illustrate CA3 areas of interest used for relative OS quantifications. (FIG. 9d) OS was significantly (*p=0.008) increased from controls after hippocampal slice cultures were exposed to SD, and this effect was abrogated when exposed to IGF-1 acutely (n=21, 12 and 9 for control, 'SD' and 'SD+IGF-1' slices, respectively). (FIG. 9e) Similarly, the significantly (*p=0.007) increased OS induced by SD was abrogated when slices were exposed to IGF-1 for 3 days prior to SD (n=21, 8 and 6 for 'SD' and 'SD+IGF-1' slices, respectively). (FIG. 9f) The significant increase in OS from SD (*p<0.001), when compared to controls, was significantly reduced (*p<0.001) in slices exposed to IGF-1 for 7 days prior to SD induction (n=21, 12 and 3 for 'SD' and 'SD+IGF-1' slices, respectively). Again, seven day treatments consisted of exposing cultures to IGF-1 for 12 hours a day for seven days. Note: IGF-1 exposure was continued for the additional 24 hour CellROX™ incubation. Scale bars=400 µm (a) and 200 µm (b and c). Comparisons between groups were made via ANOVA plus Holm-Sidak post hoc testing.

(FIG. 10a) Average current necessary to induce spreading depression (SD; i.e., SD threshold) was significantly (*p=0.018) higher when slice cultures were acutely exposed to ascorbate (AA; n=8) when compared to controls (n=12). (FIG. 10b) In contrast, average current necessary to induce SD was significantly lower (*p<0.001) when slice cultures were exposed to 50 µM hydrogen peroxide ($H_2O_2$; n=8 and 11 for control and experimental slices, respectively). (FIG. 10c) While IGF-1 triggered a significant protection from SD susceptibility (*p<0.0001) and this effect continued when co-administered with 50 µM $H_2O_2$, the higher dose of 200 µM $H_2O_2$ abrogated this effect to a non-significant difference from control. (n=14, 16, 5, 9 for control, IGF-1, IGF-1+50 µM $H_2O_2$, and IGF-1+200 µM $H_2O_2$, respectively). When compared to IGF-1, SD thresholds of controls and IGF-1+200 µM $H_2O_2$ were significantly decreased (#p≤0.00001). Comparisons between groups were made via Student's t-test (FIG. 10a, b) or ANOVA plus Holm-Sidak post hoc testing.

(FIG. 11a) Slice culture excitability in response to OS was further characterized by classifying evoked potential changes to a single current pulse that normally triggered a half-maximal field potential response where a normal field potential (FP; left) was rated "1"; a FP that included stimulus-related bursting activity (center) was rated "2"; and a stimulus that resulted in spreading depression (right) was rated is a "3". Relative evoked excitability was determined as a sum of responses seen (e.g., responses of "2" and a "3" yielded an overall excitability score of five). Responses were measured 30 minutes after exposure to hydrogen peroxide ($H_2O_2$). (FIG. 11b) Exposure to $H_2O_2$ (n=7) triggered a significant (*p<0.001) increase in evoked excitability compared to control (n=8) and this increase was abrogated by acute application of IGF-1 (n=4) to a non-significant difference from control. IGF-1 exposure alone (n=4) had no significant impact on slice CA3 area evoked excitability (i.e., showed a response of "1"). (FIG. 11c) 3-day exposure to IGF-1 had a similar impact on slice culture OS-increased excitability mimicked by application of $H_2O_2$. $H_2O_2$ significantly (*p<0.001) increased slice excitability (n=15) compared to control (n=18). Pretreatment with IGF-1 for 3 days (n=9) reduced the $H_2O_2$-induced increased excitability to a non-significant difference from control. (FIGS. 11d-e) Exemplary images of control (FIG. 11d) slice culture OS compared to increased slice OS induced by exposure to menadione (FIG. 11e). Calibration bar, 200 Dotted boxes indicate CA3 areas of interest used for relative OS quantifications (f and g). (FIG. 11f) Exposure to menadione (M; n=12) triggered a significant (*p<0.001) increase in OS compared to control (n=18). Acute treatment with IGF-1 (n=15) reduced OS from menadione to a non-significant (p=0.15) difference from control (n=18). Acute IGF-1 exposure alone (n=18) did not reduced slice culture OS from control. (FIG. 11g) Pretreatment with IGF-1 for 3 days (n=15) also reduced menadione-induced significant increase in OS (*p<0.001; n=12) to a non-significant (p=0.148) difference from control (n=15). In addition, IGF-1 pretreatment alone (n=18) significantly (*p=0.008) reduced slice culture OS compared to control.

(FIG. 12a) Exemplary recording of unstimulated control CA3 pyramidal layer spontaneous electrophysiological activity. (FIG. 12b) Exemplary recording of 3-day IGF-1-exposed CA3 pyramidal layer spontaneous electrophysiological activity. (FIG. 12c) Acute IGF-1 treatment (n=9) triggered a significant (*p=0.03) increase in spontaneous CA3 pyramidal neuron spiking compared to control (n=6). (FIG. 12d) 3-day IGF-1 treatment also (n=7) triggered a significant (*p=0.001) increase in spontaneous CA3 pyramidal neuron bursting compared to control (n=6). (FIG. 12e) Similarly, 7-day IGF-1 treatment also (n=6) triggered a significant (*p<0.001) increase in spontaneous CA3 pyramidal neuron bursting compared to control (n=7). Seven day treatments consisted of IGF-1 exposure for only 12 hours daily. Comparisons between groups made via ANOVA plus Holm-Sidak post hoc testing.

(FIG. 14A) Western blot analyses for MBP confirm that chronically applied IFN-γ (500 U/mL×24 hours) is sufficient to significantly ("*", p<0.01; n≥5 for all groups in figure) reduce MBP levels. Furthermore, co-administration of TNF-α (100 ng/mL) with IFN-γ leads to a further decline in MBP. (FIG. 14B) Importantly, removal of T cells from hippocampal slice cultures by exposure to anti-CD4 for 24 hours at 7 days in vitro, abrogates the decline in MBP that otherwise is seen after SD. Thus, confirming involvement of T cells. (FIG. 14C) Also, blockade of neutral sphingomyelinase with GW 4869 prevents the drop in MBP after SD. Taken together, these results suggest that acute, high exposure to IFN-γ [recall SD alone triggers an abrupt elevation in IFN-γ and TNF-α, among other cytokines (Kunkler et al., 2004)] triggers an abrupt elevation in TNF-α that activates sphingomyelinase which is involved in demyelination from SD.

(FIG. 15A) MBP was significantly (p<0.001) increased above baseline. (FIG. 15B) Importantly, SD susceptibility was significantly (p<0.001) increased and OS similarly reduced (FIG. 15C).

(FIG. 16C) Western blots confirm exosome-specific protein markers. IFN-γ stimulated exosomes triggered a significant rise in MBP above baseline levels (FIG. 16D), a significant reduction in SD susceptibility that was greater than a 200-fold change (FIG. 16E) as well as (FIG. 16F) a significant reduction in OS.

(FIG. 17A) Confocal imaging for glutathione (long arrow) and a microglia marker (short arrow) confirmed that pulsed exposure to IFN-γ selectively increases microglial glutathione. (FIG. 17B) Furthermore, this increase is significant (p<0.001; n≥5/group) and can be mimicked by exposure to exosomes isolated from slice cultures activated by pulsed-exposure to IFN-γ.

DETAILED DESCRIPTION OF THE INVENTION

The classic migraine episode is characterized by unilateral head pain preceded by various visual, sensory, motor symptoms, collectively known as an aura. Most commonly, the aura consists of visual manifestations such as scotomas, photophobia, or visual scintillations (e.g., bright zigzag lines). The typical headache of migraine is throbbing or pulsatile. (However, more than 50% of people who suffer from migraines report non-throbbing pain at some time during the attack.) The headache is initially unilateral and localized in the frontotemporal and ocular area, but pain can be felt anywhere around the head or neck. The pain typically builds up over a period of 1-2 hours, progressing posteriorly and becoming diffuse. The headache typically lasts from 4-72 hours. Among females, more than two thirds of patients report attacks lasting longer than 24 hours. Migraine headaches may be unilateral or bilateral and may occur with or without an aura. Migraines without aura are the most common, accounting for more than 80% of all migraines. Migraine attacks may also include visual manifestations without headache. The inventors note that migraine is not a neurodegenerative condition, thus, it is not necessary that a treatment be neuroprotective. In certain aspects neuroprotective effects can be explicitly excluded from the scope of the claims.

Diagnosis of migraine without aura, according to the International Headache Society, can be made according to the following criteria, the "5, 4, 3, 2, 1 criteria": 5 or more attacks. For migraine with aura, two attacks are sufficient for diagnosis. 4 hours to 3 days in duration. 2 or more of the following: Unilateral (affecting half the head); Pulsating; "Moderate or severe pain intensity"; "Aggravation by or causing avoidance of routine physical activity". 1 or more of the following: "Nausea and/or vomiting"; Sensitivity to both light (photophobia) and sound (phonophobia).

CSD or Spreading depression (SD) is a paroxysmal perturbation of brain that is thought to cause migraine aura, and perhaps migraine (Lauritzen and Kraig, 2005). It is classically defined as a transient loss in spontaneous and evoked electrical activity, associated with a large DC potential change in the interstitial space, which both propagate at a uniquely slow speed of about 3 mm/min (Bures et al., 1974; Somjen, 2001). SD is triggered in susceptible gray matter areas of brain where a sufficient volume is synchronously depolarized (Brazier, 1963). This triggering effect results from increased excitation, reduced inhibition, or a combination of these two effects, which results in a flurry of spontaneous discharges that immediately precede the loss in activity of SD (Mody et al., 1987; Kruger et al., 1996; Kunkler and Kraig, 1998). Furthermore, recent evidence showed that spontaneous and evoked activity is increased long after episodes of SD.

Figures 9A, 9B, 9C, 9D, 9E, 9F:
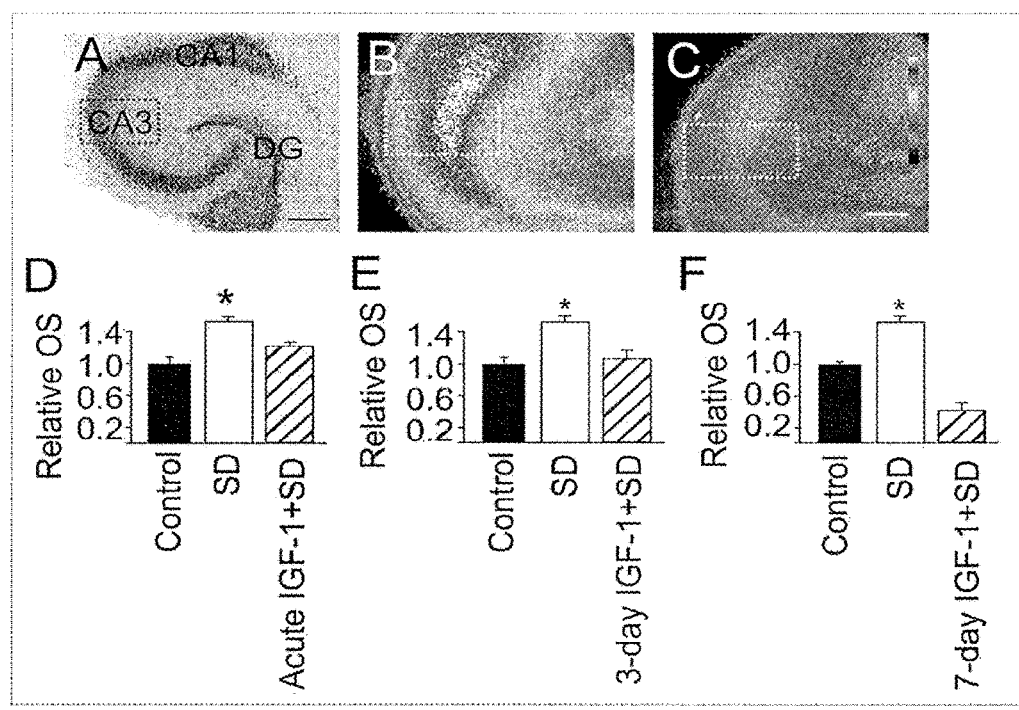
FIGS. 9a-9f IGF-1 decreased oxidative stress from spreading depression.

Evidence indicates that microglia are activated by increased synaptic activity (Ziv et al., 2006; Hung et al., 2010) and that their signaling can also influence synaptic activity (Beattie et al., 2002; Kaneko et al., 2008; Stellwagen et al., 2005; Stellwagen and Malenka, 2006). Stellwagen and coworkers show that TNF-α enhances neuronal excitation by increasing AMPA receptor cell surface expression and reducing GABA receptor membrane levels (Stellwagen et al., 2005; Stellwagen and Malenka, 2006). Furthermore, Turrigiano and colleagues show that this capacity of microglia is involved in homeostatic synaptic scaling, an adaptive response of brain directed toward tuning neural circuit activity to a functionally optimal state (Steinmetz and Turrigiano, 2010). Thus by extension, microglia are likely to be involved in SD. Indeed, SD activates microglia (Caggiano et al., 1996; Hulse et al., 2008). The inventors show that activated microglia (e.g., that produces TNF-α (Hulse et al., 2008); FIG. 2) or oxidative stress (Grinberg et al., 2012 a, b; FIG. 9) increase spreading depression susceptibility.

Microglial motion reflects their activation state. Within the context of disease, microglia travel directionally toward sites of irreversible injury (McGlade-McCulloh et al., 1989). In contrast, within healthy brain tissue, microglial somata remain in place, but during increased synaptic activity their processes extend and retract at an increased rate (Nimmerjahn et al., 2005). Since SD is preceded by a flurry of increased synaptic activity (Brazier, 1963; Kruger et al., 1996; Kunkler and Kraig, 1998) followed by a brief period of electrical silence during SD, and then long afterwards, a persistent increase in synaptic activity.

The inventors contemplate that immune cells are activated (and influence other cells) by contact-mediated effects as well as by paracrine signaling. The inventors probed for microglial cell motion associated with SD using vital imaging of microglia in mature rat hippocampal slice cultures. The results show that a fraction of microglia in control slice cultures moved in a stereotypic fashion consistent with Levy flights. Furthermore, hours after SD, the number of microglia moving long distances was significantly increased. The inventors asked whether this effect could be mimicked by alterations in synaptic activity. Synaptic activity increased by activation of microglia (with lipopolyssacharide (LPS)) as well as neuronal activity increased by chemical long-term potentiation (cLTP) significantly decreased the number of microglia moving long distances. In contrast, blockade of synaptic activity via exposure to tetrodotoxin (TTX) significantly increased the number of microglia moving long distances and this increase could be abrogated by co-incubation with glutamate and adenosine triphosphate (ATP), two paracrine mediators released with synaptic activity, for which microglia have receptors.

Recently the study of cell movements from the perspective of a random walk has attracted great interest (Berg, 1993; Li et al., 2008; Reynolds, 2010a; Reynolds, 2010b; Selmeczi et al., 2008; Selmeczi et al., 2005; Takagi et al., 2008). These studies have focused on the movements of cells in culture or over surfaces. The inventors provide evidence to show that microglia travel via Levy flights. Moreover, the inventors show that these movements correspond to the type of Levy flight that has been associated with an optimal random search pattern (Cabrera and Milton, 2004; Viswanathan et al. 1999). The inventors contemplate that microglial migration after SD is a means by which these cells influence a wider expanse of brain either by contact or by paracrine signaling, perhaps to increase regional susceptibility to SD, and by extension, migraine.

In one aspect, novel therapeutics and therapeutic methods are provided that prevent recurrent migraine and its transition to chronic migraine.

Interferon-gamma (IFN-γ) is a cytokine produced by T-lymphocytes and natural killer cells, and is the only member of the type II class of interferons. This interferon was originally called macrophage-activating factor, a term now used to describe a larger family of proteins to which IFN-γ belongs. In humans, the IFN-γ protein is encoded by the IFNG gene. IFN-γ has been shown to interact with Interferon gamma receptor 1. An example of an IFN-γ amino acid sequence is found in GenBank accession number AAB59534 (GI:184639), which is incorporated herein by reference as of the filing date of this application. Certain aspects are directed to isoforms and variants of IFN-γ that retain one or more functions of IFN-γ, particularly the therapeutic effects described herein. IFN-γ peptides or polypeptides can comprise all or part of an amino acid sequence similar to that provided in GenBank accession number AAB59534, which is incorporated by reference and which is SEQ ID NO:1.

Interleukin 11 (IL-11) is a member of a family of growth factors that includes growth hormone, granulocyte colony-stimulating factor (G-CSF), and others. IL-11 is also a member of a family of cytokines that includes IL-6, leukemia inhibitory factor (LIF), oncostatin M (OSM), and ciliary neurotrophic factor (CNTF), which all signal through a common receptor subunit, gp130. IL-11 is naturally produced by bone marrow stromal cells, and is a thrombopoietic growth factor that, in conjunction with other factors, stimulates the proliferation of hematopoietic stem cells and megakaryocytic progenitor cells and induces maturation, resulting in increased platelet production. IL-11 is also known under the names adipogenesis inhibitory factor (AGIF) and oprelvekin. In humans, the IL-11 protein is encoded by the IL11 gene. Interleukin 11 has been shown to interact with the interleukin 11 receptor, in addition to gp130. An example of an IL-11 amino acid sequence is found in GenBank accession number NP_000632 (GI:10834994), which is incorporated herein by reference as of the filing date of this application. Certain aspects are directed to isoforms and variants of IL-11 that retain one or more functions of IL-11, particularly the therapeutic effects described herein. IL-11 peptides or polypeptides can comprise all or part of an amino acid sequence similar to that provided in GenBank accession number NP_000632, which is incorporated by reference and which is SEQ ID NO:2.

Insulin-like growth factor 1 (IGF-1) is also known as somatomedin C or mechano growth factor, and has also been referred to as a "sulfation factor" or "nonsuppressible insulin-like activity" (NSILA). The insulin-like growth factor family includes two ligands, IGF-1 and IGF-2, two cell membrane receptors, IGF-1R and IGF-2R, and six IGF-1-binding proteins IGFBP1-6. In humans, the IGF-1 protein is encoded by the IGF1 gene. Insulin-like growth factor 1 has been shown to interact with the IGF-1 receptor (IGF1R), and the insulin receptor. An example of an IGF-1 amino acid sequence is found in GenBank accession number CAA01955 (GI:4529932), which is incorporated herein by reference as of the filing date of this application. Certain aspects are directed to isoforms and variants of IGF-1 that retain one or more functions of IGF-1, particularly the therapeutic effects described herein. IGF-1 peptides or polypeptides can comprise all or part of an amino acid sequence similar to that provided in GenBank accession number CAA01955, which is incorporated by reference and which is SEQ ID NO:3.

Insulin is a hormone central to regulating carbohydrate and fat metabolism in the body. Insulin is synthesized in the pancreas within the β-cells of the islets of Langerhans. Insulin has also been shown to be produced within the brain. The proinsulin precursor of insulin is encoded by the INS gene. Insulin has been shown to interact with the insulin receptor. An example of an insulin amino acid sequence is found in GenBank accession number AAA59172 (GI: 386828), which is incorporated herein by reference as of the filing date of this application. Certain aspects are directed to isoforms and variants of insulin that retain one or more functions of insulin, particularly the therapeutic effects described herein. Insulin peptides or polypeptides can comprise all or part of an amino acid sequence similar to that provided in GenBank accession number AAA59172, which is incorporated by reference and which is SEQ ID NO:4.

Peptides and/or polypeptides described herein may possess deletions and/or substitutions of amino acids relative to the native sequence. Sequences with amino acid substitutions are contemplated, as are sequences with a deletion, and sequences with a deletion and a substitution. In some embodiments, these polypeptides may further include insertions or added amino acids.

Polypeptides that may be administered include those that have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990 or 1000 contiguous amino acids, or any range derivable therein, of SEQ ID NO:1, SEQ ID NO:2, SEQ ID NO:3, or SEQ ID NO:4. Alternatively, the polypeptide in compositions or methods may be 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range derivable therein, identical to SEQ ID NO:1, SEQ ID NO:2, SEQ ID NO:3, or SEQ ID NO:4.

The following is a discussion based upon changing of the amino acids of a peptide and/or polypeptide to create a library of molecules or a second-generation molecule. For example, certain amino acids may be substituted for other amino acids in a polypeptide without appreciable loss of function, such as ability to interact with a target peptide sequence. Since it is the interactive capacity and nature of a polypeptide that defines that polypeptide's functional activity, certain amino acid substitutions can be made in a polypeptide sequence and nevertheless produce a polypeptide with like properties.

In making such changes, the hydropathic index of amino acids may be considered. The importance of the hydropathic amino acid index in conferring interactive function on a protein is generally understood in the art (Kyte and Doolittle, 1982). It is accepted that the relative hydropathic character of the amino acid contributes to the secondary structure of the resultant protein, which in turn defines the interaction of the protein with other molecules.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. However, in some aspects a non-conservative substitution is contemplated. In certain aspects a random substitution is also contemplated. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Pharmaceutical compositions described herein comprise an effective amount of interferon-gamma, interleukin 11, insulin-like growth factor 1, insulin or a combination thereof and/or additional agents dissolved or dispersed in a pharmaceutically acceptable carrier. The phrases "pharmaceutical" or "pharmacologically acceptable" refers to molecular entities and compositions that do not produce an adverse, allergic or other untoward reaction when administered to an animal, such as, for example, a human, as appropriate. The preparation of a pharmaceutical composition that contains interferon-gamma, interleukin 11, insulin-like growth factor 1, insulin or a combination thereof or additional active ingredients will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or similar regulatory bodies.

In certain embodiments, the active compound, e.g., interferon-gamma, interleukin 11, insulin-like growth factor 1, insulin or a combination thereof, may be formulated for intranasal administration. Nasal administration of the present invention may comprise the use of a nasal spray which uses water or salt solutions as the liquid carrier with peptide or polypeptide being dispersed or dissolved in the water in a therapeutically effective amount. In another embodiment, a permeation enhancer is emulsified in the aqueous phase that contains the active compound. The emulsification may be effected through the use of one or more suitable surfactants. Any suitable surfactant or mixture of surfactants can be used in the practice of the present invention, including, for example, anionic, cationic, and non-ionic surfactants. Examples of non-ionic surfactants are PEG-60 corn glycerides, PEG-20 sorbitan monostearate, phenoxy-poly(ethyleneoxy)ethanol, sorbitan monooleate, and the like. In general the surfactant is present in an amount less than about 4, 3, 2, 1.5, 1, 0.5, 0.2% (w/w) the composition, including all values and ranges there between. In another embodiment, the surfactant may be present in amounts less than about 1.5% (w/w), less than about 1.3% (w/w), less than about 1% (w/w), or less than about 0.3% (w/w). For examples see PCT/US2009/046438, specifically incorporated herein by reference in its entirety.

In certain embodiments, the pharmaceutical compositions may be formulated as eye drops, intranasal sprays, inhalants, and/or as other aerosols. Methods for delivering compositions directly to the nasal passage or lungs via nasal aerosol sprays has been described in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid or liquid particles dispersed in a liquefied or pressurized gas propellant. A typical aerosol for inhalation may consist of a suspension of active ingredients in liquid propellant or a mixture of liquid propellant and a suitable solvent. Suitable propellants include hydrocarbons and hydrocarbon ethers. Suitable containers may vary according to the pressure requirements of the propellant. Administration of the aerosol may vary according to a subject's age, weight and the severity and response of the symptoms.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

Embodiments may comprise different types of carriers depending on whether it is to be administered in solid, liquid or aerosol form, and whether it needs to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing a target directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

Compounds may be formulated into a composition in a free base, neutral or salt form. Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions may be administered in a manner compatible with the dosage formulation and in such amount as is therapeutically effective. The formulations may be easily administered in a variety of dosage forms such as formulated for parenteral administrations such as injectable solutions, or aerosols, or formulated for alimentary administrations such as drug release capsules and the like.

Methods and compositions that are suitable for administration may be provided in a pharmaceutically acceptable carrier with or without an inert diluent. The carrier should be assimilable and includes liquid, semi-solid (i.e., pastes), or solid carriers. Except insofar as any conventional media, agent, diluent or carrier is detrimental to the recipient or to the therapeutic effectiveness of the composition contained therein, its use in an administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In some embodiments, the composition is combined with the carrier in any convenient and practical manner (i.e., by solution, suspension, emulsification, admixture, encapsulation, absorption and the like). Such procedures are routine for those skilled in the art.

In a further embodiment, the composition is combined or mixed thoroughly with a semi-solid or solid carrier. The mixing can be carried out in any convenient manner such as grinding. Stabilizing agents can be also added in the mixing process in order to protect the composition from loss of therapeutic activity (i.e., denaturation in the stomach). Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, methods may concern the use of pharmaceutical lipid vehicle compositions that include interferon-gamma, interleukin 11, insulin-like growth factor 1, insulin or a combination thereof, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods described herein.

One of ordinary skill in the art would be familiar with the range of techniques that can be employed for dispersing a composition in a lipid vehicle. For example, the composition comprising interferon-gamma, interleukin 11, insulin-like growth factor 1, insulin or a combination thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition that is administered to a subject can be determined by physical and physiological factors such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, about 2%, about 5%, about 10%, about 15%, about 20%, about 25%, about 30%, about 35%, about 40%, about 45%, about 50%, about 55%, about 60%, about 65%, about 70%, about 75%, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 1, 5, 10, 20, 30, 40, 50, 60, 70, 80 mg/kg/body weight to about 50, 60, 70, 80, 90, 100, 150, 200 mg/kg/body weight, about 5 microgram/kg/body weight to about 500 milligram/kg/body weight, etc., can be administered, based on the numbers described above.

In some embodiments, the compositions of the present invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, e.g., gum tragacanth, acacia, cornstarch, gelatin or combinations thereof; an excipient, e.g., dicalcium phosphate, mannitol, lactose, starch, magnesium stearate, sodium saccharine, cellulose, magnesium carbonate or combinations thereof; a disintegrating agent, e.g., corn starch, potato starch, alginic acid or combinations thereof; a lubricant, e.g., magnesium stearate; a sweetening agent, e.g., sucrose, lactose, saccharin or combinations thereof; a flavoring agent, e.g., peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

In further embodiments, the composition of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,753,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards or other regulatory bodies.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the active compound, i.e., interferon-gamma, interleukin 11, insulin-like growth factor 1, insulin or a combination thereof, may be formulated for administration via various miscellaneous routes, for example, transdermal administration.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate absorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the compositions and methods of the present invention involve a therapeutic composition comprising a compound that reduces, ameliorates, or prevents migraine. These compositions can be used in combination with a second therapy to enhance the therapeutic effect of a first and/or second therapy. These compositions would be provided in a combined amount effective to achieve the desired effect. This process may involve providing or administering a first therapy and a second therapy at the same or different time. This may be achieved by administering one or more compositions or pharmacological formulations that includes or more of the agents, or by contacting the cell with two or more distinct compositions or formulations, wherein one composition provides (1) a first therapy comprising administering TNF-α pathway effector, such as interferon-gamma, IL-11, IGF-1 insulin, or a combination thereof; and/or (2) a second therapy. A second therapy may be administered that includes analgesics, such as aspirin, caffeine, vasoconstrictors, narcotics, 5HT1 receptor agonist (e.g., sumatriptan, naratriptan, rizatriptan, zolmitriptan, eletriptan, almotriptan and frovatriptan), other anti-migraine drugs, and combinations thereof. Several antimigraine drugs are known. See, e.g., U.S. Pat. Nos. 4,650,810, 4,914,125, 4,916,125, 4,994,483, 5,021,428, 5,200,413, 5,242,949, 5,248,684, 5,273,759, 5,317,103, 5,364,863, 5,399,574, 5,434,154, 5,441,969, 5,464,864, 5,466,699, 5,468,768, 5,491,148 and 5,494,910, each of which is incorporated herein by reference in its entirety. Antimigraine drugs most commonly used in treatment of migraine fall into the following groups: ergot alkaloids, beta-blocking agents, calcium channel blocking agents, antidepressants, selective 5-HT1 agonists, sedatives, local anesthetics, adrenergic blocking agents and mixtures of these.

It is contemplated that one may provide a patient with the first therapy and the second therapy within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In certain embodiments, a course of treatment (i.e., a first therapy, or a first therapy in combination with a second therapy) will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one or more therapies may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and a second therapy can be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the subject may be given one or multiple administrations of a first and/or second therapy. Moreover, after a course of treatment, it is contemplated that there is a period of time at which no treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed, for example a first therapy is "A" and a second therapy is "B":

A/B/A B/A/B B/B/A A/A/B A/B/B B/A/A A/B/B/B B/A/B/B

BBB/A BB/AB A/A/B/B AB/AB A/B/B/A B/B/A/A

B/A/B/A B/A/A/B A/A/A/B B/A/A/A A/B/A/A A/A/B/A

Administration of any compound or therapy of the present invention to a subject will follow general protocols for the administration of such compounds or therapies, taking into account the toxicity, if any, of the vector or any protein or other agent. Therefore, in some embodiments there is a step of monitoring toxicity that is attributable to combination therapy. It is expected that the treatment cycles would be repeated as necessary. It also is contemplated that various standard therapies may be applied in combination with the described therapy.

Therapeutic agents of the invention can be administered in doses of 0.01, 0.05, 0.01, 0.5, 1, 2, 3, 4, 5, 6, 7, 8, 9, 10, 20, 30, 40, 50, 60, 70, 80, 90, 100, 200 pg, ng, µg, or mg per dose or per kilogram of subject body weight, including all values and ranges there between.

Components and compounds of the invention can be provided to a subject at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more times as part of a therapy or treatment. Moreover, it is contemplated that there may be a course of therapy prescribed, and that the course may be repeated, if necessary.

In other embodiments, components or compounds of the invention are provided separately to the patient. It is contemplated that subject is provided with first agent and a second agent is provided or administered within 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 day and/or 1, 2, 3, 4, 5, 6, 7, 8, 9, 10, 11, 12 weeks, or any range derivable therein. Consequently, a subject may take or be provided a first or second component or compound of the invention 1, 2, 3, 4, 5, 6, 7, 8, 9, 10, 11, 12, 13, 14, 15, 16, 17, 18, 19, 20 or more times each, or any range derivable therein, within a specified time period of being provided a first or second component or compound.

In some embodiments a polypeptide, such as IL-11, IFN-γ, IGF-1 or insulin is not provided directly to the patient or to cells of the patient, and instead, the patient is provided with an expression vector that comprises a nucleic acid sequence encoding the polypeptide under the control of a promoter, wherein the polypeptide is expressed in a cell containing the vector. Consequently, embodiments involving polypeptides may be implemented with an expression vector to achieve a treatment for migraine patients. There are two basic approaches to such a therapy, (i) ex vivo gene expression and (ii) in vivo gene expression.

In ex vivo gene expression, cells are removed from a subject and transfected with a desired gene in vitro. The genetically modified cells are expanded and then implanted back into the subject. Various methods of transfecting cells such as by electroporation, calcium phosphate precipitation, liposomes, microparticles, and other methods known to those skilled in the art can be used in the practice of the present invention.

In in vivo gene expression, the desired gene is introduced into cells of the recipient in vivo. This can be achieved by using a variety of methods known to those skilled in the art. Such methods include but are not limited to, direct injection of an expression vector and introduction of an expression vector in a carrier such as a virus, liposome, or exosome.

Various transduction processes can be used for the transfer of nucleic acid into a cell using a DNA or RNA virus. In one aspect of the present invention, a retrovirus is used to transfer nucleic acid into a cell. Exogenous genetic material encoding a desired gene product is contained within the retrovirus and is incorporated into the genome of the transduced cell. In other aspects, exogenous genetic material encoding a desired gene product is contained within the virus and is maintained in the cytoplasm of the transduced cell. The amount of gene product that is provided in situ is regulated by various factors, such as the type of promoter used, the gene copy number in the cell, the number of transduced/transfected cells that are administered, and the level of expression of the desired product. The expression vector of the present invention may include a selection gene, for example, a neomycin resistance gene, to facilitate selection of transfected or transduced cells.

Expression vectors can be comprised in viruses, such as retroviruses. Replication-deficient viruses are incapable of making infectious particles. Genetically altered viral expression vectors are useful for high-efficiency transduction of genes in cultured cells and are also useful for the efficient transduction of genes into cells in vivo. Standard protocols for the use of viruses to transfer genetic material into cells are known to those skilled in the art. For example, a standard protocol can be found in Kriegler (1990) and Murray (1991).

The expression vector may also be in the form of a plasmid, which can be transferred into the target cells using a variety of standard methodologies, such as electroporation, microinjection, calcium or strontium co-precipitation, lipid mediated delivery, cationic liposomes, and other procedures known to those skilled in the art.

The present invention also provides methods for in vivo gene therapy. An expression vector carrying a heterologous gene product is injected into a recipient. In particular, the method comprises introducing a targeted expression vector, i.e., a vector which has a cell- or tissue-specific promoter.

Embodiments also concern kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and device for accomplishing nasal administration of a composition to a subject at risk of developing, having, or beginning to have a migraine. In other embodiments, a subject kit may comprise pre-filled ampules of a peptide or other pharmaceutical composition, optionally formulated as a lyophilized composition, for use with a delivery device.

Kits may comprise a container with a label. Suitable containers include, for example, bottles, vials, and test tubes. The containers may be formed from a variety of materials such as glass or plastic. The container may hold a composition which includes a peptide or polypeptide that is effective for therapeutic or non-therapeutic applications, such as described above. The label on the container may indicate that the composition is used for a specific therapy or non-therapeutic application, and may also indicate directions for in vivo or in vitro use, such as those described herein. The kit of the invention will typically comprise the container described above and one or more other containers comprising materials desirable from a commercial and user standpoint, including buffers, inhalers, cartridges, diluents, filters, needles, syringes, and package inserts with instructions for use.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

IFN-γ has detrimental and beneficial brain effects, consistent with physiological conditioning hormesis. IFN-γ exacerbates demyelination from experimental autoimmune encephalomyelitis (EAE), a model of multiple sclerosis. Yet, low-level IFN-γ before the onset of disease protects against demyelination, an effect involving an oligodendrocyte oxidative stress response (OSR). Also, spreading depression (SD) triggers a transient (1 and 3 but not 7 day) drop in myelin basic protein (MBP) in rat hippocampal slice cultures (HSC); and demyelination increases SD susceptibility in vivo.

Since T-cells are present in hippocampal slice cultures (HSC) and SD increases their production of IFN-γ, the inventors examined how T-cells and IFN-γ affect SD susceptibility. Results were based on n≥3-6/group and comparisons made v. shams.

PCR arrays show a 3.61 fold increase in osteopontin and a 2.22 fold decrease in IL-10, which indicates an enhanced Th1 effect from SD. Exposure to the Th1 cytokine IFN-γ (500 U/mL) triggers significantly increased susceptibility to SD at 1 day but, importantly, resulted in a significantly reduced susceptibility at 3 days. Removal of IFN-γ by depletion of T-cells by anti-CD4 prevented altered susceptibility to SD and prevented the SD-induced demyelination, which otherwise triggered ruptured myelin sheaths, shown via electron microscopy (EM). Neocortical SD in vivo triggered a similar reduction in MBP a day later.

Three day treatment with IFN-γ (500 U/mL) significantly reduced reactive oxygen species generated from chemical long-term potentiation (cLTP), a physiological means to increase brain excitability like that seen hours after SD. This beneficial effect of low-level IFN-γ is supported by results from rats. In rats, enrichment, which occurs with hippocampal learning, led to a significant elevation in hippocampal T-cells, IFN-γ and MBP.

The results show SD acutely activates T-cells and overwhelms brain OSR, resulting in increased susceptibility to SD and demyelination. These effects can be prevented via treatment with IFN-γ, which modulates immune parameters that favor a Th1-skewed response extended over time. These results support the use of IFN-γ as a therapy for migraine.

Example 2

Cytokines are likely to be involved in spreading depression (SD), a well-accepted model of migraine pathogenesis. Recurrent SD significantly lowers subsequent SD threshold via TNF-α signaling. Also, cold-preconditioning is neuroprotective via low-level production of TNF-α from microglia. Importantly, production of IL-11 from neurons dampens this protective effect. The inventors focused on potential interrelations of oxidative stress (OS) and IL-11, since SD generates OS and IL-11 has antioxidant properties.

Experiments were performed in rat hippocampal slices cultures and SD induced as previously described (Pusic et al., 2011). Results were derived from n≥3-6/group. Pretreatment with minocycline significantly reduced SD susceptibility, further supporting a role for microglia in SD. Importantly, both acute and chronic (three-day) treatment with IL-11 (100 ng/mL) significantly reduced SD susceptibility. Importantly, cLTP, a cellular model of learning, significantly reduced SD susceptibility. Treatment of slice cultures with IL-11 for 3 days significantly reduced OS generated from physiological activation of the cultures via cLTP compared to shams. This is consistent with the neural activity increase seen after SD, which mimics the hyperexcitability evident in migraine patients. IL-11 reduced SD susceptibility through mechanisms that include OSR signaling. Furthermore, whole animal experiments involving environmental enrichment (i.e., increased volitional physical, intellectual, and social activity), which occurs with increased brain activity, resulted in increased IL-11 mRNA and protein, supporting the notion that increased exercise may help prevent migraine by altering neural OSR via IL-11. These results support the use of IL-11 as a therapy for migraine.

Example 3

Environmental enrichment not only protects hippocampus, but also reduces seizure susceptibility, both effects that occur with increased learning. Such learning is known to occur with increased CA3 area pyramidal neuron bursting. The inventors found that CA3 area pyramidal neuron bursting in hippocampal slice cultures (HSC) reduced susceptibility to spreading depression (SD), the most likely cause of migraine aura and perhaps migraine (Lauritzen and Kraig, 2005; Benedict et al., 2004).

This prompted the inventors to examine whether insulin could reduce SD susceptibility by increasing CA3 pyramidal neuron bursting. The inventors induced SD trans-synaptically in rat HSC using electrical stimuli (100 μs pulses @ 10 Hz for 1 s) ranging from 1 to 10,000 nC in order to determine SD threshold in sham and experimental groups (Pusic et al., 2011). Results were based on n≥3-6/group. Insulin (400 μg/mL) exposure for three days triggered a significant reduction in SD susceptibility. This insulin dose approximates the pharmacological levels seen in humans treated with nasal insulin. However, the inventors found that IGF-1 was much more effective, producing results when administered at 40 ng/mL. The inventors hypothesized that the effect of insulin occurred through IGF-1 receptor crosstalk. IGF-1 significantly reduced SD susceptibility both acutely and after three days of treatment. This effect of IGF-1 did not involve a change in TNF-α mRNA levels two hours after SD evoked every 7-9 minutes for an hour. In contrast, three day IGF-1 treatment leads to a significant reduction in OS from cLTP, a physiological means to increase brain excitability like that seen hours after SD. These results support the use of IGF-1 and/or insulin as a therapy for migraine.

Example 4

SD is the most likely cause of migraine aura and pain (Lauritzen and Kraig, 2005). Neocortical and hippocampal SD triggers a significant increase in nociceptive activation of the caudal trigeminal nucleus (TGN). For the purposes of this example, the inventors focused on hippocampal SD since it is known to occur in uninjured human brain and it is the brain area most susceptible to SD.

The paradigm for eliciting neocortical or hippocampal SD consists of triggering SD by local KCl or electrical stimuli in rostral neocortex or hippocampus respectively. The occurrence of SD is confirmed with a DC potential recording electrode placed in the caudal neocortex or hippocampus respectively.

Immunostaining for c-fos serves as a functional marker for nociceptive activation in the TGN. c-fos positive cells in the TGN can be detected after 2 hours of SD triggered every 9 min.

Experiments were performed in HSC since this in vitro preparation closely parallels its in vivo counterpart. Cultures were initially grown in a horse serum-based media (Kunkler and Kraig, 1997) and after 18 days in vitro (DIV) some cultures were transferred to a serum-free media based on Neurobasal and Gem-21 (Mitchell et al., 2010, Mitchell et al., 2011). SD was induced by bipolar electrical stimulation in the dentate gyrus and SD confirmed by recording its DC change in the CA3 area. SD showed the typical DC changes. Baseline activity increased with a flurry of activity after stimulation to trigger SD followed by a loss in spontaneous or evoked activity before SD recovery.

SD occurs with increased cytokine production, which some consider a consequence and not a cause of the malady. However, microglial TNF-α increases AMPA and decreases GABA receptors, which alters excitability. The mechanisms responsible for this are not understood. Since vascular T-cells become activated in migraineurs (Empl et al., 1999) and activated T-cells enter brain (Engelhardt and Ransohoff, 2005), the inventors explored whether T-cells may induce an upstream change that influences SD susceptibility by signaling between neurons and glia. Since T-cells can live up to a year (Empl et al., 1999) but perhaps less in brain, the inventors probed for their presence in HSC (18-35 DIV) where environmental conditions can be controlled and single cells followed in space and time.

After an hour of SD, slices were allowed to recover for 2 hours and then harvested for total RNA isolation and PCR amplification of cytokine targets. The extraction strategies produced high quality intact RNA as determined via a gel that showed sharp RNA bands. Next, dilution curve amplifications of primers were checked to be sure primers produced uniform amplification differences. For example, optimal amplifications show a uniform increase in Ct thresholds. In contrast, amplifications are not uniform with defective primers.

The inventors first probed for increased TNF-α mRNA expression and found that SD induced a significant ($P<0.001$) 2-20 fold rise in TNF-α mRNA (n=6/group). These positive samples were used for PCR array screening. Next, PCR array technology was used as a means more sensitive than traditional gene chips to look for evidence of T-cells in adult hippocampal slice cultures. The gene expression screen for inflammatory cytokine changes was completed by RT² Profiler™ PCR Arrays.

Several cytokine targets suggested T-cells may be present in mature slices. The inventors looked for the presence of T-cells using CD6 labeling. The inventors found that ~56 T-cells were positive for CD6 in individual slice cultures. CD6 marked T-cells can be visualized by via confocal microscopy, cell diameters are about 5-6 μm.

IFN-γ is thought to be expressed predominantly, if not soley, by T-cells in brain. Thus, the fact that IFN-γ mRNA could not be detect after SD seemed odd, especially since the inventors previously detected a modest but significant change in IFN-γ protein (via bead-based ELISA assays) after SD (Kunkler et al., 2004).

Since only ~50 T-cells are found in a slice culture (out of ~100,000 total cells), the inventors used the SAB RT² nano PreAMP cDNA Synthesis Kit as a means to detect potential ultra-low level expression of IFN-γ. This means of cDNA preamplification provided a 12-fold increase in sensitivity to RNA levels. The results illustrate the capacity of preamplification to increase detection sensitivity. Ct threshold for the housekeeper, Rpl13a, was 20.5 with initial amplification and this was increased to 14.1 with use of the preamplification kit, a 12-fold increase corresponding to 12 cycles of PCR amplification of cDNA. In parallel, IFN-γ in control cultures was not detectable but was well within detection range with preamplification.

Next, the inventors probed for evidence of IFN-γ production after slice exposure to lipopolyssacharide (LPS) and found it in 5-6 μm cells consistent with a T-cell morphology. Furthermore, the inventors found that IFN-γ mRNA rose by 4.66 fold with 2 hours SD elicited every 9 min for an hour.

Goddard and coworkers (Goddard et al., 2007) show that MHC expression, necessary for T-cell activation, changes with neural activity on neurons. Furthermore, activated astrocytes and especially microglia also present MHC. Thus, SD (or migraine) may activate T-cells and their interactions with neural cell MHC may initiate excitability changes directly or via hormetic immune signaling (Kraig et al., 2010). If so, T-cells, and their activation behavior, may be ideal targets for development of novel therapeutics to mitigate episodic migraine and prevent chronic migraine.

Example 5

Chronic migraine (CM) is a prevalent healthcare burden whose pathogenesis remains incompletely defined. Evidence suggests that central sensitization involving increased expression of pro-inflammatory mediators and alterations in the periaqueductal gray are involved (Aurora, 2009). However, increased migraine frequency also correlates with the transformation of episodic migraine (EM) to CM (Silberstein and Olesen, 2005)).

Central sensitization and alterations of the periaqueductal gray may be "downstream" signaling phenomena of CM while recurrent spreading depression (SD) is the "upstream" neural signaling change. This conclusion is based on several facts. First, SD may trigger both migraine aura and pain since it is sufficient for nociceptive activation of the trigeminal nuclei and periaqueductal gray. Second, SD can inhibit neuronal firing in the brainstem and facilitate trigeminovascular activation, further suggesting its involvement in CM. Third, SD initiates pro-inflammatory changes within involved brain. Astrocytes and microglia show reactive changes for weeks after recurrent SD. Importantly, SD also triggers increased production of eicosanoids and innate cytokines, including TNF-α, Interleukin-1 beta (IL-1β) and potentially IFN-γ principally involving microglia. These signaling molecules are involved in somatosensory central sensitization and thus may have a similar functional impact on SD.

Increasing evidence indicates that TNF-α has particular involvement in activity-dependent signaling function within brain. Malenka and coworkers show that physiological levels of TNF-α increase AMPA receptor membrane expression and reduce GABA receptor expression there. Our work and that of others indicate that increased brain activity associated with environmental enrichment (i.e., increased social, physical and intellectual opportunities) occurs with increased expression of TNF-α. Furthermore, the neuroprotective effects of environmental enrichment requiring TNF-α can be amplified by eicosanoids and involve activation of microglia, which generate the TNF-α. In contrast to high-dose acute TNF-α effects from disease which are toxic, these activity-dependent low-dose physiological TNF-α changes improve brain function and require time to develop.

The inventors contemplate that the greater TNF-α change from SD (compared to that seen from learning), while non-toxic, is sufficiently high to be maladaptive and over time triggers the increased excitability seen after recurrent SD and migraine. The latter occurs via alterations in AMPA and GABA receptor membrane expression and function. Accordingly, the inventors examine the degree to which microglia and TNF-α expression alter brain excitability from recurrent SD.

Figures 1A, 1B:
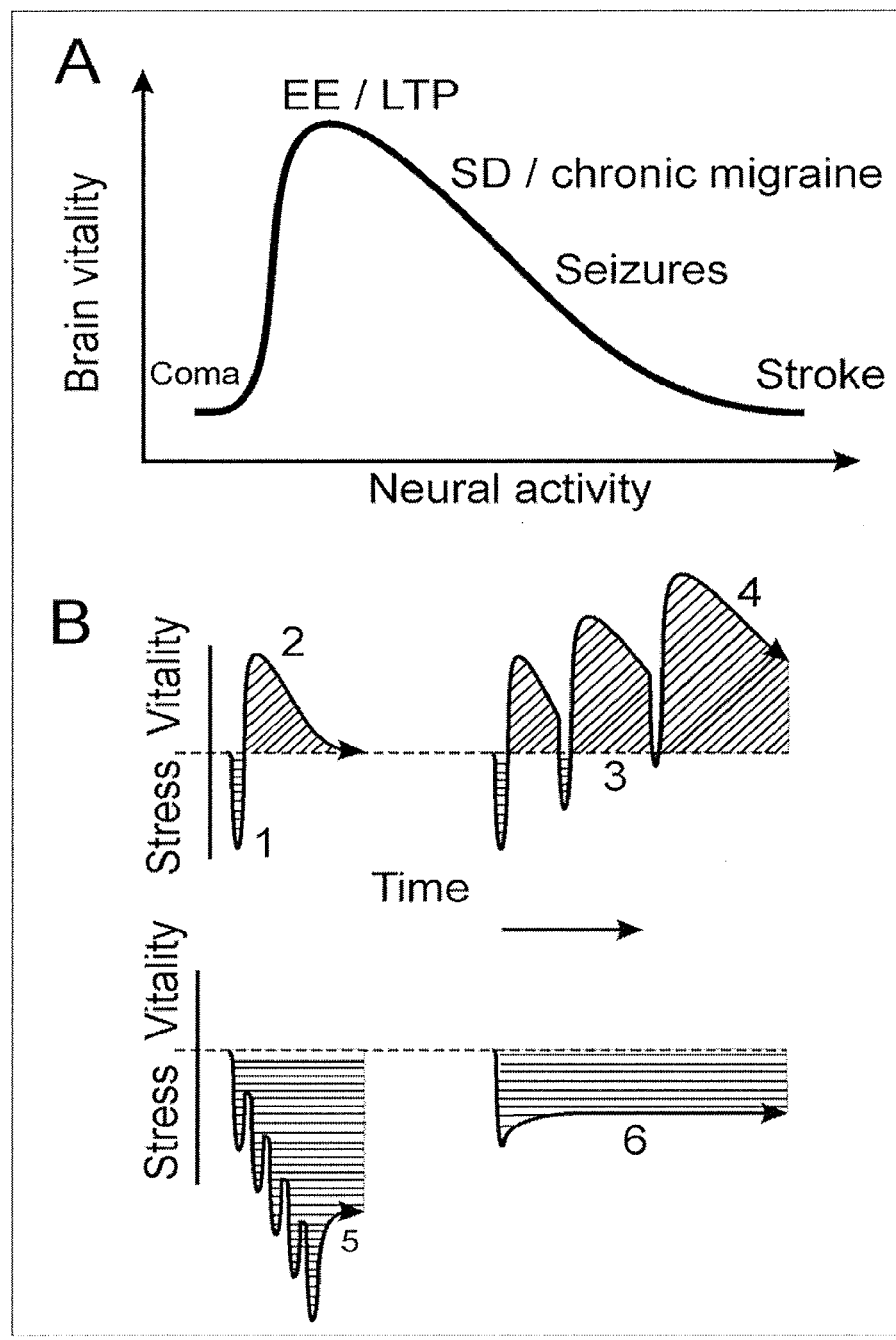
FIGS. 1A-1B. Illustrates an outline of a suggested pattern of increased brain vitality versus neural activity (FIG. 1A and FIG. 1B). Irritative (e.g., TNF-α, IL-11, IGF-1, or IFN-α) initiative stimuli (1) and adaptive response (2) that, when delivered phasically reduces SD susceptibility (3-4). With recurrent activating stimuli (3) and sufficient time (4), brain increases its resilience to disease. Maladaptive changes within brain may ensue when irritative stimuli occur without sufficient time to allow for adaptive nutritive changes (5) or become constant (6), for example, as can occur with high frequency or chronic migraine.

Slice cultures were prepared and maintained as previously described (Mitchell et al., 2010a,). After 18 days in vitro (DIV), slice cultures were transferred to serum-free media that included additional calcium and magnesium. Cultures were screened at 21 DIV to ensure no pyramidal neuron death was present. Standard electrophysiological recordings were performed by placing a slice culture insert in a PDMI recording chamber with controlled temperature and pH (FIG. 1). The recording chamber was aerated with 5% $CO_2$-balance air at 36° C. and media flowing at 1.2 mL/min or was held static around the slice culture insert. A recording electrode was placed at the CA3 pyramidal cell layer and a stimulating electrode was placed at the surface of the dentate gyrus. Recordings were initiated prior to placing the stimulating electrode on the culture to ensure no spreading depression was triggered as a result.

Studies began with determination of the current needed to maximize standard CA3 area field potential responses. This documented the normalcy of evoked synaptic responses between preparations. If a slice's field EPSPs were not at least 3-4 mV, it was discarded.

Next, trans-synaptically evoked SD was determined. Here, the inventors stimulated slices via the dentate gyrus with 100 μs pulses delivered at 10 Hz for 1 sec every 1-2 minutes at increasing μA current intensities until SD occurred. This proved to be a most sensitive means to establish the threshold for synaptically driven SD.

Considerable effort was expended in establishing a slice culture media that provides healthy cultures to 35 days in vitro, easily elicits SD, and allows detection of low-level immune signaling. Slice cultures maintained in horse serum-based media are almost always resistant to SD induction. The inventors found this to also be true for a media that contained 20% horse serum, Neurobasal A, B-27, insulin and ascorbate. A robust CA3 area field potential response and ability to trigger SD was, however, rarely seen. Instead, triggering pulses for SD commonly evoked bursting.

The inventors tested SD susceptibility in cultures grown in serum free media (based on Neurobasal and either B-27 or Gem-21 (Chen et al., 2008) that also included ascorbate. Evoked field potentials were analogous to those in horse serum-based media. SD could easily be stimulated in the serum free media. Furthermore, SD significantly lowered the threshold for subsequent SD triggered three days later.

Figures 2A, 2B, 2C, 2D, 2E:
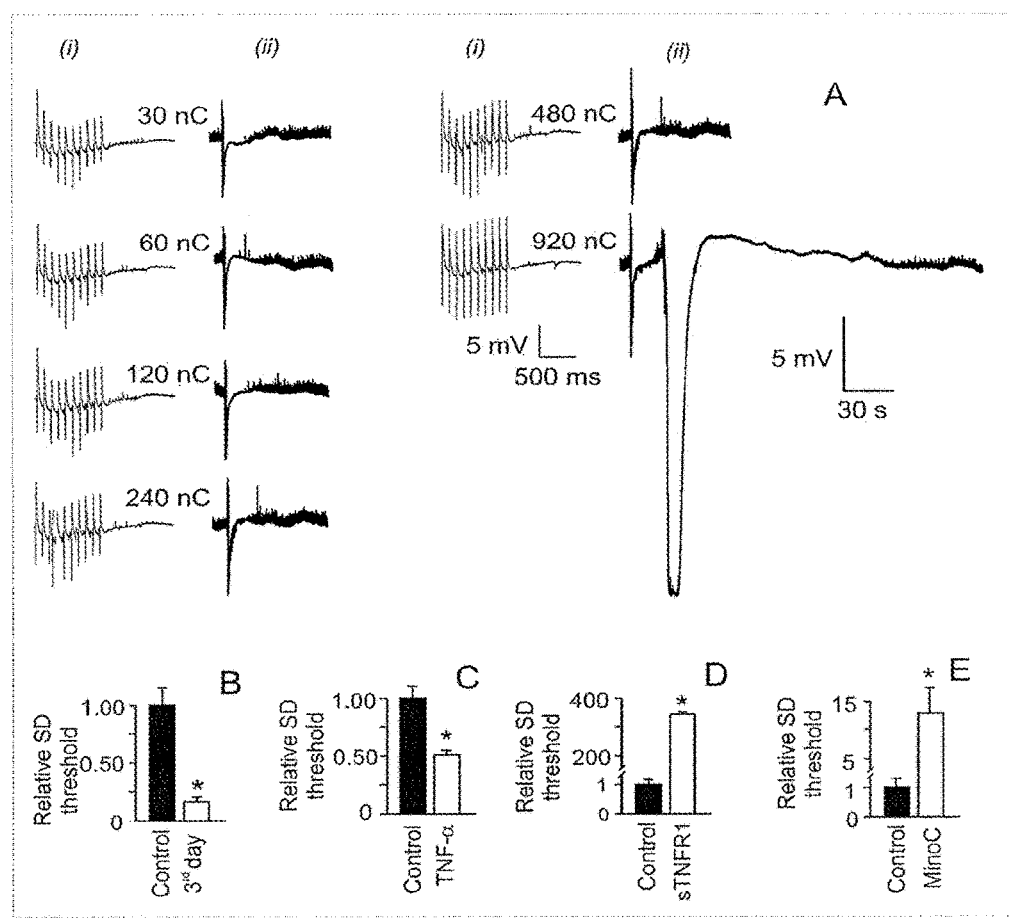
FIGS. 2A-2E. SD-induced increased susceptibility to SD.

The inventors determined that TNF-α was involved in SD susceptibility (FIG. 2D). For example, exposure to TNF-α (100 ng/mL) for 3 days significantly lowered the threshold for SD compared to that needed in other cultures on first exposure to SD stimuli (FIG. 2D). Furthermore, the increased susceptibility to SD triggered by previous SD could be abrogated by removal of TNF-α signaling by treatment with soluble TNFR1 (200 ng/mL) after the first day of SD (FIG. 2E).

Microglia are the predominant, if not the sole, source of TNF-α in non-injured brain. Thus, taken together our results demonstrate that SD, and therefore migraine, involves microglia and their low-level production of the pro-inflammatory cytokine TNF-α.

SD and TNF-α are involved in improving brain function via preconditioning neuroprotection. Thus, involvement of TNF-α in increasing SD susceptibility may seem contradictory. However, the basic tenets of hormetic signaling explain this apparent contradiction of microglial-TNF-α signaling in brain.

A hormetic (or U-shaped) dose response pattern consists of low-level stimulation and high-level inhibition that involves two basic tenets. First, an irritative (or stress) stimulus must be of sufficient magnitude. Second, sufficient time must elapse for adaptive changes to occur that result in a nutritive effect (FIG. 1).

FIG. 1 outlines our suggested pattern of increased brain vitality versus neural activity (A and B). Irritative [(FIG. 2B); e.g., TNF-α, IL-11, IGF-1, insulin, or IFN-γ)] stimuli (1). Adaptive processes are (2). With recurrent activating stimuli (3) and sufficient time (4), brain increases its resilience to disease.

Maladaptive changes within brain may ensue when irritative stimuli occur without sufficient time to allow for adaptive nutritive changes (5) or become constant (6). The inventors contemplate that such neuroimmune signaling from microglia and TNF-α may be involved in the transformation of episodic migraine to chronic migraine. Deciphering the SD-dependent innate cytokine signaling within brain will identify therapeutic targets to prevent episodic and chronic migraine.

Example 6

Neuronal activity necessarily increases brain TNF-α (from microglia) and IFN-γ (from T-cells) levels as well as oxidative stress (OS) (from oxidative metabolism). In turn, these small molecules and OS can increase neuronal activity. If neuronal activity becomes excessive (i.e., as occurs after recurrent SD), SD susceptibility will increase. Accordingly, the inventors define the interrelated roles of TNF-α, IFN-γ, and OS in promoting SD susceptibility. The inventors use an SD model in rat hippocampal slice cultures and rats in vivo. SD susceptibility is compared to measurements of net OS, specific antioxidants, and critical OS signaling system changes. OS-related gene expression changes are assessed using PCR arrays and proteomic changes are assessed using multiplexed-ELISAs and immunostaining. Cell-specificity of relevant mRNA and protein changes are determined using laser dissection microscopy and double-label immunostaining, respectively. The inventors examine the impact of inhibiting critical OS signaling points on SD susceptibility.

The inventors have established a highly reliable in vitro model showing that SD-induced increased SD susceptibility depends on TNF-α from activated microglia. (FIG. 2).

Figures 3A, 3B, 3C:
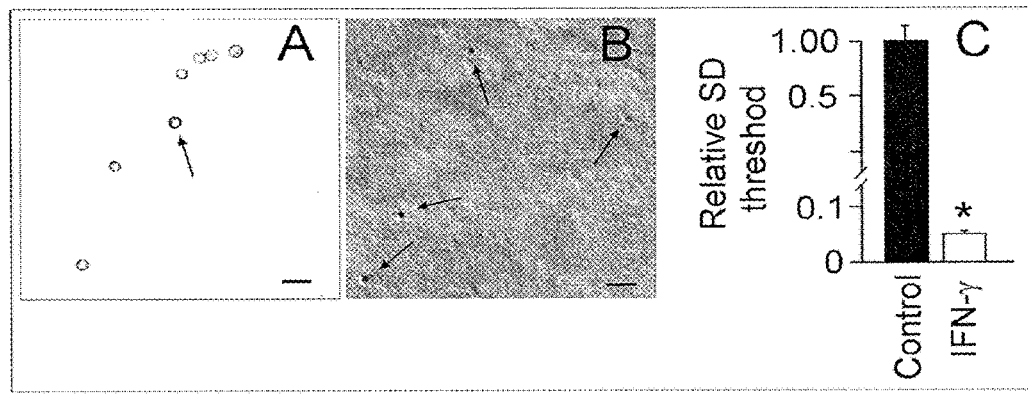
FIGS. 3A-3C. T-cells in slice cultures produce IFN-γ, which acutely increases SD susceptibility.

Using PCR array technology, the inventors discovered that the slice cultures contain Th1 T-cells (Pusic and Kraig, 2010). Since vascular T-cells become activated in migraineurs (Empl et al., 1999) and activated T-cells enter brain (Engelhardt and Ransohoff, 2005), the inventors began exploring whether T-cells induce an upstream change that influences SD susceptibility. The results show that T-cells become activated after SD in slice cultures and increase their production of IFN-γ, which acutely increases SD susceptibility (FIG. 3). Thus, slice cultures are well-suited for study of T-cell signaling of SD.

Figures 4A, 4B, 4C, 4D, 4E, 4F:
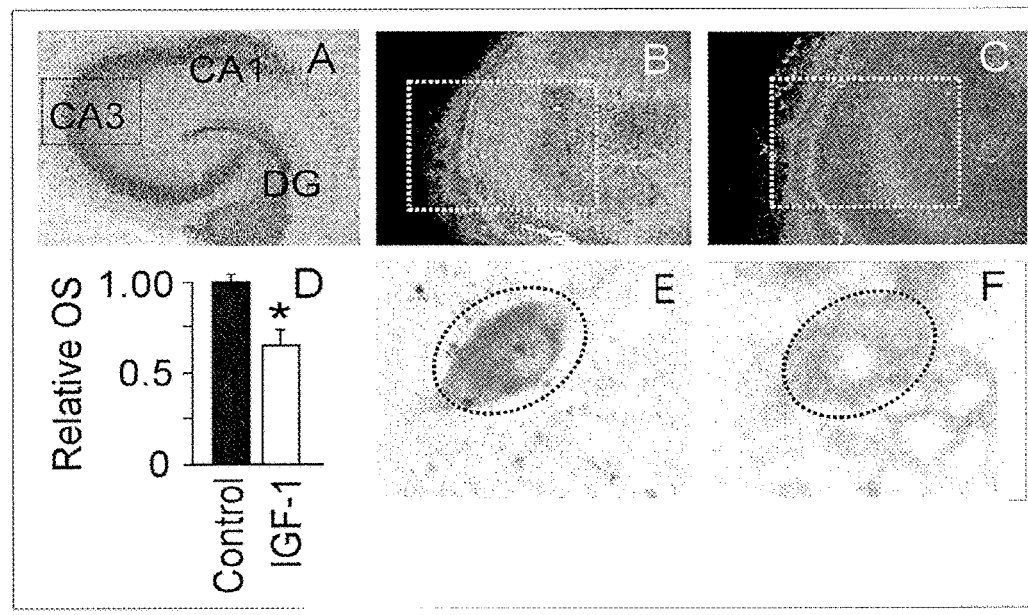
FIGS. 4A-4F Oxidative stress (OS) from SD and its reduction by IGF-1.

IFN-γ from T-cells is believed to play a crucial role in immune-mediated demyelinating disease (Popko et al., 1997; Imitola et al., 2005; Lees and Cross, 2007). SD triggers an acute, but transient, disruption of myelin that is associated with a significant reduction in myelin basic protein (MBP) after 1 and 3 days (Kunkler et al., 2006). Using immunostaining, the inventors have confirmed that this drop in MBP is also seen in vivo 1-2 days after SD. Furthermore, oligodendrocytes are highly sensitive to OS (Lin et al., 2008; Juurlink et al., 1998) and SD increases OS, a finding the inventors have confirmed occurs in slice cultures (FIG. 4). Finally, removal of T-cells by exposure to anti-CD4 (0.1 mg/mL) at 7 days for 24 hours completely prevented SD-induced increased susceptibility to SD versus control >21 days later in slice cultures (p=0.964; n=6/ea. group).

Slice cultures are prepared, maintained, and induced to fire SD as previously described using trans-synaptic excitation of CA3, where SD is initiated (FIG. 4) (Kunkler et al., 2005; Pusic et al., 2011). Though others assess changes in excitatory and inhibitory synaptic drive via evoked field potential analyses, the inventors agree with the Dudek laboratory that this approach is less reliable (Waldbaum and Dudek, 2009; Shao and Dudek, 2009). Instead, measurement of the relative neural circuit excitability (as used by the inventors for SD susceptibility) is preferable.

The inventors compare SD susceptibility to innate cytokine, OS, critical nodes of OS signaling, and antioxidant levels. Determination of this seemingly wide array of parameters is now comfortably accomplished using multiplexed assays. The inventors use multiplexed PCR arrays (from SABiosciences) and multiplexed flow cytometric assays [(MFCAs) for proteins; from Bio-Rad and Millipore]. Laser dissection microscopy and double-label immunostaining are used for specific cell-type-enhanced measurements of RNA and protein, respectively.

Cytokine, IGF-1, and antioxidant screening is done first using PCR arrays that contain wells for: (1) cytokines (TNF-α, IFN-γ), their cognate receptors; (2) IGF-1 and a principal IGF-1 binding protein involved in brain signaling, IGFBP-3 (Jogie-Brahim et al., 2009; Carro et al., 2000); and (3) antioxidants [MnSOD (manganese superoxide dismutase), CuSOD (copper superoxide dismutase), catalase, GSH (glutathione), peroxiredoxin, thioredoxin, NQO-1 (NAD(P)H dehydrogenase quinone 1), and HO-1 (heme oxygenase 1)]. Significant mRNA changes (i.e., ≥2-fold) are verified by MFCAs and immunostaining for corresponding protein production. In addition, MFCAs are used to assess changes in phosphoprotein kinases (GSK3β and eIF2α) and transcription factors (ATF-4 and Nrf2) critical to OS signaling.

The inventors use double-label immunostaining and digital image quantification procedures that are standard in their lab to confirm the cellular origin of cytokine-OS signaling molecule changes (Mitchell et al., 2010; Mitchell et al., 2011). Laser dissection microscopy procedures follow those established in the inventors laboratory (Hulse et al., 2008). Laser dissection mRNA samples are prepared as previously described (Hulse et al., 2008). However, inventors now utilize a nano-preamplification system from SABiosciences that allows detection of low-expression RNAs (e.g., from ~50 cells in 100,000) (Pusic et al., 2011). This sensitivity will allow detection of cytokine-antioxidant mRNA measurements from specific brain cell types, as the inventors have done for T-cells in slice cultures (Pusic et al., 2011; Pusic and Kraig, 2010).

OS signaling inhibition. Optimal doses of inhibitors are determined by a paradigm successfully used by the inventors (Pusic et al., 2011) and others (Romera et al., 2004). First, initial doses will be derived from published in vitro studies or manufacturer's recommendations. The inventors apply doses 10× below and above these values to test for toxicity in slice cultures. At least 1 day is necessary to allow for the adaptive changes that require protein synthesis induced by ischemia tolerance or enriched environment (EE) (Pusic et al., 2011; Kraig et al., 2010). These effects persist for several days to weeks. Thus, use of a 3-day adaptive paradigm allows for experiment efficiency and is of sufficient duration to preclude any toxic effects of signaling cascade modulation from chronic alterations. This is consistent with the notion that phasic application of EE-like signaling (e.g., from IL-11, IFN-γ, IGF-1, insulin) is likely to be optimal. Three days are used here as a single cycle of the phasic paradigm. For negative controls, heat inactivated inhibitors are applied at previously determined doses (Hulse et al., 2008). The inventors also modeled more prolonged EE-like conditions using seven-day treatments of IGF-1 where IGF-1 was given for only 12 hours daily as well as treating with IFN-γ for only 12 hours once a week. Sham controls consist of exposure to vehicle alone. Sham controls consist of exposure to vehicle alone.

The inventors will inhibit critical node OS signaling using established pharmacological and siRNA strategies. To inhibit eIF2α dephosphorylation, the inventors will apply sal003 (10 µM, hippocampal slice culture) (Costa-Mattioli et al., 2007). Pharmacological blockade of Nrf2 is accomplished by application of brusatol (40 nM, cultured cell line) (Ren et al., 2011). Inhibition of GSK3β can be accomplished through use of either lithium chloride (LiCl, 2 mM, cultured hippocampal neurons) (Mendes et al., 2009) or thiadiazolidinone-8 (TDZD-8, 1 µM, primary brain microvascular endothelial cells) (Ramirez et al., 2010). Accell siRNA reagents targeting these genes in mouse and in rat are commercially available from Thermo Scientific, and are used according to the manufacturer's specifications (Pusic et al., 2011). Accell Red Non-targeting siRNA are used to demonstrate cellular transfection.

The inventors will analyze data using SigmaStat (v. 3.5) software. All data will be tested for normality (P value to reject: 0.05) and equal variance (P value to reject: 0.05). Control data will be normalized to 1.00 per experiment with related group results scaled proportionally to facilitate inter-experiment comparisons. All experimental groups will include sham controls. Results are expressed as mean±SEM. Power analysis is used to determine adequacy of sample size. Two technical replicates are used for mRNA and protein assays and 5 or more biological replicates are used for all slice culture experiments. Behavioral testing is completed with n=15/group. ANOVA with post hoc Holm Sidak testing (or where applicable, Student's t-test) is used to test for significance (i.e., $p<0.05$).

The stimulation paradigm is to trigger 1, 3 or 6 SDs and measure threshold to SD responses 1, 3, 7 and 14 days later as shown in FIG. 2. Sham controls consist of firing half-max field potentials via 100 µs single pulses instead of SD and then assessing SD threshold 1, 3, 7 and 14 days later (FIG. 2).

In certain studies, the stimulation pattern is the same as described above with measurements of (a) tissue and (b) cell-type-specific OS changes 1, 3, 7 and 14 days after SD. The same cultures can be used for both sets. Cell-specific measurements are done using 20 µm sections, confocal microscopy, and double-label staining (FIG. 4, 13). Since oligodendrocytes are highly sensitive to OS, and our work shows MBP falls shortly after recurrent SD, the inventors will also measure MBP as a potential functional marker of 0 S. In further studies the stimulation pattern is to evoke 6 SDs over an hr with (a) multiplexed mRNA measurements of cytokines, receptors, and antioxidants using PCR arrays. Again, significant changes in tissue mRNA is confirmed by (b) laser dissection microscopy for specific cell-enhanced mRNA changes and (c) multiplexed ELISAs for confirmation of protein expression. Double-label immunostaining is used for cell type identification. (d) Changes in the phosphorylation state of tissue OS signaling-related kinases and transcription factors are measured by multiplexed ELISAs. (e) The cellular origin of significant changes is verified with double-label immunostaining. Measurements of mRNA species are made 2 hours after SD and proteins 1, 3, 7, and 14 days after SD. Shams and controls (described above) are included.

In still further studies, the experimental paradigm is to evoke 6 SDs over an hr and harvest tissue 3 days later. The inventors will inhibit key points of the SD-OS signaling system and measure resultant changes in (a) SD susceptibility, (b) OS levels, and (c) antioxidant protein levels. Inhibition is accomplished at the cytokine (TNF-α and IFN-γ) level using sTNFR1 and anti-CD4. Inhibition of key kinases (Nrf2, eIF2α, and GSK3β) is accomplished as described above. Inhibitors will be applied the day before and maintained during SD, until harvest. Excessively long inhibition of OS pathways can be deleterious, as can excessive OS. Three day exposures [i.e., to TNF-α, sTNFR1, anti-IFN-γ, anti-CD4, IL-11, IFN-γ, IGF-1, as the inventors show (FIG. 8)] are long enough for adaptive changes (e.g., involving protein synthesis) to occur without triggering irreversible cell injury and are short enough to be consistent with phasic signaling of EE.

In certain studies the same paradigm as described above (1, 3, and 6 SD) is performed in vivo (hippocampus and neocortex) to establish the next translational step in application of cytokine-OS signaling for migraine therapeutics. After SD susceptibility measurements 1, 3, 7, and 14 days later, brains are harvested for measurement of OS using a carbonyl assay kit for oxidized proteins (Shin et al., 2008). The paradigm producing the greatest change in susceptibility is repeated, and tissue harvested a day later for MBP quantification.

The inventors expect that the acute susceptibility change for SD and associated OS from SD will show a linear or threshold (and not hormetic) response. This conclusion is based on preliminary data and the assumption that adequate time would not have elapsed for adaptive production of increased antioxidant proteins needed to dampen hyperexcitability of SD. The inventors also expect that specific brain cell types will show differential OS level changes, thus requiring measurements (preferably multiplexed) at the level of specific brain cell types. Cellular responses are varied and dose-dependent, with fewer cells responding at a lower dose (Tay et al., 2010). Even within a homogeneous culture, cells do not uniformly respond to TNF-α activation. Accordingly, brain with four different principal cell types (plus vascular endothelial cells), can be expected to show similarly heterogeneous responses to cytokines (and OS), that are likely to be interactive. Pretreatment with IFN-γ protects microglia from OS via upregulation of MnSOD (Chen et al., 2009) and astrocytes prevent neuronal death from OS (Rohl et al., 2008). Additionally, activated microglia influence the expression of antioxidants in astrocytes (Correa et al., 2011). Finally, a recent study shows that SD inversely correlates with cortical myelin content (Merkler et al., 2009), indicating the importance of oligodendrocytes in SD susceptibility. The inventors' data directly extend this finding from a model of demyelinating disease to showing that recurrent SD itself can be demyelinating.

OS signaling is also likely to show differential cellular changes. Synaptic activity boosts intrinsic antioxidant activity in neurons (Papadia et al., 2008) and eIF2α plays a critical role in neuronal synaptic activity associated with memory and learning (Costa-Mattioli et al., 2005; Costa-Mattioli et al., 2009; Gkogkas et al., 2010) and OS signaling in oligodendrocytes (Lin et al., 2008). Nrf2 plays an important role in responding to astrocytic OS (Haskew-Layton et al., 2010). The role of these factors in microglia is less clear and whether all (including GSK3β) are involved is unknown. The mechanism for how specific cell types are responsible for production of certain antioxidants in response to SD is unclear. The inventors expect OS (and related downstream signaling and antioxidant production) will show neural cell type heterogeneity, with perhaps the greatest change occurring in microglia and astrocytes, compared to neurons and oligodendrocytes.

Cytokines can also be expected to show differential cell type changes. T-cells are the main, if not sole, source of IFN-γ, while TNF-α is produced under physiological conditions by microglia (Hulse et al., 2008), and IL-11 mostly by neurons, and to a lesser extent, astrocytes (Mitchell et al., 2011). IGF-1, on the other hand, often comes from the periphery (Jogie-Brahim et al., 2009) but can also be produced by astrocytes and neurons. Cognate receptors for these mediators are also differentially expressed among brain cell types.

In vivo studies will parallel culture results since the slices closely parallel the in vivo counterpart. The data support this suggestion by showing that MBP decreases 1-2 days after 1 hr of recurrent SD in animal neocortex, a finding first established in slices. To show that measurements are not unique to hippocampus parallel measurements will be made after neocortical SD.

Example 7

Enriched environment (EE) reduces hyperexcitability from seizures (Kraig et al., 2010; Young et al., 1999), SD (Guedes et al., 1996), and migraine (Darabaneanu et al., 2011) through adaptive signaling. However, the EE signaling that prevents development of increased susceptibility to SD is unknown. The inventors contemplate that low levels of IL-11, IFN-γ, and IGF-1, small molecules involved in neuroprotection from preconditioning, are also involved in EE, and follow a hormetic pattern. IL-11, IFN-γ, IGF-1, and OS have interrelated roles in reducing SD susceptibility via EE. Studies using EE, EE+SD and SD+EE are modeled in hippocampal slice cultures, with their results confirmed in vivo using EE+SD in rats. The experimental endpoint of altered SD susceptibility from EE is compared to measurements of net OS, specific antioxidant levels, and changes in critical OS signaling molecules. Measurements follow those described above, extended to include confirmation via behavioral testing of EE efficacy. The overall expected outcome is to define the signature of small molecules critical for OS signaling by which EE reduces SD susceptibility. This provides novel information on how EE enhances naturally occurring means to prevent increased susceptibility to SD from SD, and by extension, high frequency and chronic migraine (HFCM).

Adaptive (i.e., hormetic) signaling requires that (a) an initiating stimulus be sufficiently robust to evoke an adaptive response and (b) sufficient time must elapse for adaptive responses to occur. For our purposes, the initiating activity-dependent stimuli (EE) are the pro-inflammatory cytokines TNF-α from microglia (Kraig et al., 2010) and IFN-γ from T-cells, which trigger adaptive responses.

Adaptive signaling from EE includes production of IL-11, IFN-γ, and IGF-1. IL-11 is an anti-inflammatory cytokine localized to neurons, and to a lesser extent, astrocytes (Mitchell et al., 2010; Mitchell et al., 2011). TNF-α stimulates the production of IL-11, which in turn inhibits TNF-α production (Mitchell et al., 2010; Mitchell et al., 2011). T-cells, the main if not sole source of IFN-γ under physiological brain conditions, play a role in the nutritive effect of EE on brain. Increased numbers of T-cells enter brain parenchyma with EE (Ziv et al., 2006). Furthermore, T-cells are involved in the maintenance of neurogenesis and spatial learning (Ziv et al., 2006), effects our data show require IFN-γ. Circulating IGF-1 mediates the neuroprotective effects of exercise (Carro et al., 2000), likely via activity-dependent entry of IGF-1 from the periphery (Nishijima et al., 2010). However, ischemic brain injury triggers expression of IGF-1 in neurons and astrocytes (Hwang et al., 2004), and these cells may also be a source of IGF-1 from EE. Furthermore, IGF-1 can increase brain excitability (Nunez et al., 2003; Ramsey et al., 2005) and thus may play a role in the increased activity of EE. Finally, IGF-1 impacts OS since GSK3β is the main downstream effector of IGF-1 signaling. In each case, these small molecules (i.e., IL-11, IFN-γ, and IGF-1) stimulate the production of antioxidants, which increase with neuronal activity (Papadia et al., 2008). The inventors contemplate that activity-dependent increased antioxidant levels are an important means by which EE can reduce SD susceptibility (Guedes et al., 1996), and by extension migraine (Darabaneanu et al., 2011). Our data support this conclusion.

Figures 5A, 5B, 5C:
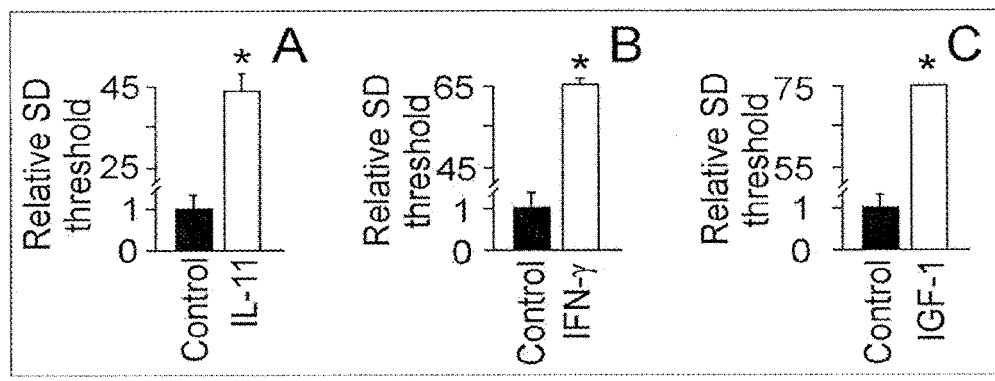
FIGS. 5A-5C Reduced SD susceptibility by small molecules that mimic enriched environment (EE). Slice cultures were exposed to agents for 3 days and then SD susceptibility determined. IL-11 (100 ng/mL) provided significant (p=0.001; n=9 and 6, respectively) (FIG. 5A) as did IFN-γ (500 U/mL; p<0.001; n=9 and 6) (FIG. 5B) and IGF-1 (40 ng/mL; p<0.001; n=8 and 7) (FIG. 5C).

The inventors show that IL-11, IFN-γ, and IGF-1 significantly reduced SD susceptibility after 3 days of pretreatment (FIG. 5), effects that reduce OS (FIGS. 4, 9, 10, 13, 15, 16). Furthermore, EE (which increases MBP) and cLTP (an in vitro model of learning used here) both significantly raise the threshold for SD. EE in C57BL/10J mice triggered a significant (2 and 2.2-fold, respectively) rise in IFN-γ and IL-11 mRNA. Similarly, cLTP in slices triggered an 89-fold rise in IL-11 mRNA 2 hours after stimulation.

Slice cultures are used for EE, EE+SD and SD+EE with groups and measurements per experiment as described above, except as noted below. The experimental paradigm will be to: evoke cLTP and then a day later, trigger SD (i.e., 1, 3, or 6), followed by measurements taken 1, 3, or 7 days later. Note: 14 day measurements after SD are excluded since the cultures are used from 21-35 days in vitro. The endpoints are to compare SD susceptibility after EE to innate cytokine, OS, critical nodes of OS signaling, and antioxidant levels.

The inventors use a well-accepted method for inducing cLTP in slice cultures (Kraig et al., 2010; Otmakhov et al., 2004a; Otmakhov et al., 2004b; Kopec et al., 2006). The protocol consists of raising cAMP levels and increasing synaptic activity using rolipram/forskolin applied in a $Mg^{2+}$-free Ringer's solution (36° C.) for 5 min, then allowing slices to recover in normal media.

For EE, rats (12/cage) are housed in a Marlau-style enrichment cage with free access to food and water, an array of toys, running wheel, and socialization bowl that are changed weekly for 4 weeks to provide increased volitional opportunities for intellectual, physical, and social stimulation (i.e., EE). NE rats are housed in single standard cages.

Hippocampal and neocortical SD will be induced in isoflurane-anesthetized rats as previously described for rats using nanoliter injections of 0.5 M KCl (or 0.5 M NaCl for sham controls) every 9 minutes for 1 hr (Kunkler and Kraig, 2003) for acute SD, SD after EE or SD after EE signaling mimics.

A visual recognition task is used to test hippocampus-dependent memory, since it is non-stressful. Ability to recognize a novel versus familiar object is a measure of hippocampus-dependent memory (Clark et al., 2000; Gobbo and O'Mara, 2004; Mansuy et al., 1998; Mumby et al., 2002; Rampon et al., 2000; Ruby et al., 2008; Rutten et al., 2008; Thuret et al., 2009).

Figure 7A:
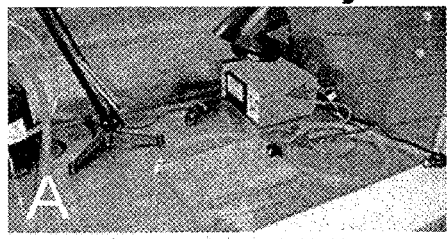
FIGS. 7A-7C Nasal administration of IGF-1, IL-11, IFN-γ, and insulin significantly (p<0.001) reduced SD susceptibility. Images show experimental setups for nasal administration and testing.
Figure 7B:
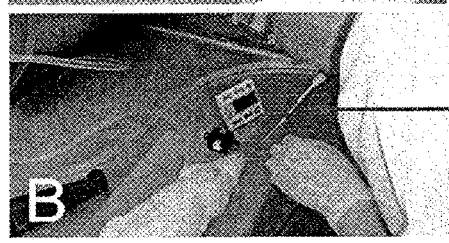
Figure 7C:
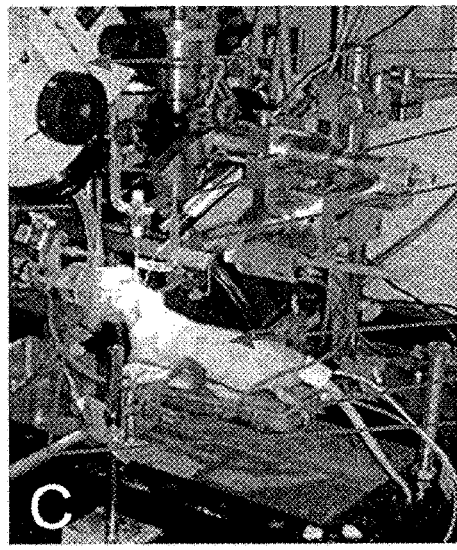

Methods will follow those outlined above, except that SD will be preceded by EE (i.e., cLTP). Certain studies will include SD followed by EE. The inventors will mimic our targeted EE signaling variables (i.e., IL-11, IFN-γ, and IGF-1) by applying them for 3 days, as shown in FIG. 7. Initial concentrations will be as previously described (FIG. 5) as well as 0.1× and 10× of those doses. The latter will also include SD threshold measurements.

To ensure that EE enhanced hippocampus-dependent memory, animals are behaviorally tested. The threshold for SD, OS, and antioxidant levels will be measured 1, 3, 7, and 14 days later. The behavioral testing paradigm should not interfere with cytokine and OS signaling since it is non-stressful. Controls versus EE alone will verify this.

While the process of reducing susceptibility to SD from activity associated with EE is likely to be hormetic, the inventors contemplate that the dose-response of SD susceptibility and OS change from EE will show a linear or threshold dose-response pattern that is higher than those seen in the absence of EE.

The inventors expect that specific brain cell types will show differential OS level changes. However, such changes are likely to be reduced as a result of EE. This suggests that the numbers (or diversity) of cell types responding are reduced, as illustrated by the differential responses of primary cultures to lower doses of TNF-α (Tay et al., 2010).

In vivo results should parallel in vitro slice results. As noted above, hippocampal slice cultures closely resemble the structure and function of their in vivo counterpart. To-date, our results of SD susceptibility, cellular responses to SD [e.g., astrogliosis, microgliosis, and now oligodendrocyte dysfunction (reduced MBP)], and OS are comparable between preparations.

Example 8

Figure 6:
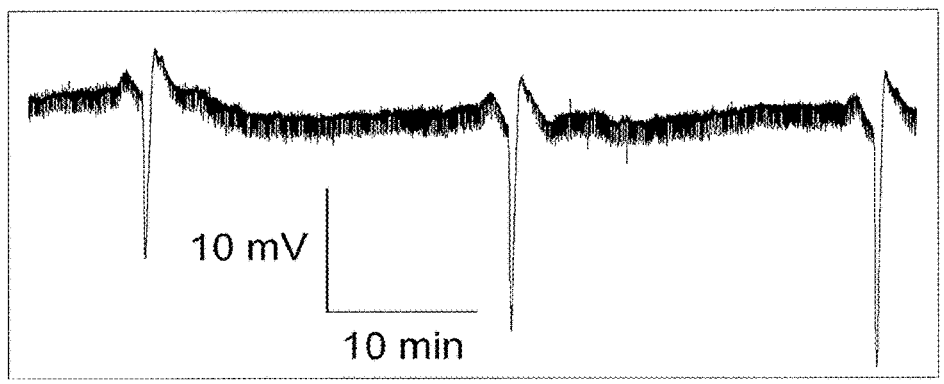
FIG. 6. A whole animal recording paradigm was used determine the threshold for SD in neocortex and hippocampus from anesthetized rat, with exemplary SDs shown.

Nasal insulin enters brain (Born et al., 2002) and improves cognitive function (Stockhorst et al., 2004; Hallschmid et al., 2008)—therefore it could be used as a mimetic of EE. If insulin can effectively mimic EE, the inventors contemplate that other small molecules may exert a similar effect. In fact, considerable evidence demonstrates that nasally delivered IGF-1 enters brain (Thorne et al., 2004) and significantly improves brain function after injury (Liu et al., 2001). Since other small molecules have also been shown to enter brain and mediate a therapeutic impact (Akpan et al., 2011; De Rosa et al., 2005), the inventors expect that IL-11 and IFN-γ does as well. Accordingly, the inventors define the degree to which their small molecules (IL-11, IFN-γ, and IGF-1) enter brain and reduce SD susceptibility and OS. The inventors used ratas for hippocampal and neocortical SD (FIGS. 6-7).

Rats (FIGS. 6 and 7) are anesthetized with inhalational isoflurane and kept warm. While anesthetized, animals are placed in a supine position and 50 μL of sterile drug (i.e., IFN-γ, IGF-1, or IL-11) solution [or sterile saline vehicle (sham control)] is administered nasally by delivering 5 μL alternating between the left and right naris every 2 min over 20 minutes. Animals are given nasal drug treatments daily at the same time for 7 days before subsequent experiments. Doses for all 3 agents begin with the effective doses noted in our work using slice cultures (1×), then include others (0.1× and 10×). The inventors base this strategy on the fact that the effective culture dose for IGF-1 (40 ng/mL) closely approximates the dose used in vivo (143 μg/kg).

Inventors will detect delivery of EE-mimicking agents via immunostaining. Human recombinant IFN-γ, and human recombinant IGF-1 are identified via monoclonal antibodies (Nishijima et al., 2010). Since there is no antibody specific to human recombinant IL-11 that will not cross-react with mouse or rat, biotinylated IL-11 is administered and detected with an anti-biotin antibody.

In certain studies, agents will be delivered via nasal administration daily for seven days before experiments. On the 8th day, initial SD threshold will be determined and 1, 3, or 6 SDs will be induced. This will be followed by measurement of SD threshold [and OS] 1, 3, 7, and 14 days later. SD will be evoked and measurements made separately in hippocampus and neocortex.

In other studies a high dose of antioxidant (100× vitamin C) is administered for 4 weeks (i.e., "anti-EE"), then measuring threshold to first SD, then elicit 1, 3, or 6 SDs followed by measurements of SD threshold and OS 1, 3, 7, and 14 days later. Again, the studies are performed in hippocampus and neocortex.

The small molecule agents (IL-11, IFN-γ, IGF-1) may have equal impact on reducing SD susceptibility since nasal delivery of IGF-1 comparably increases IGF-1 in various brain regions such as hippocampus and neocortex (Thorne et al., 2004). Furthermore, given the similar molecular size of the other agents, their entry into brain should be comparable to that seen with IGF-1. Given the comparable efficacy of these three agents in preventing increased susceptibility to SD in vitro, they will show similar efficacy in vivo.

A whole animal recording paradigm was developed to determine the threshold for SD in neocortex and hippocampus from anesthetized rat. FIG. 6 below illustrates this capacity.

This approach was applied to measurement of SD threshold (FIG. 10) after treatment (FIG. 7) with nasally administered IGF-1 (150 μg), IL-11 (1 μg), IFN-γ (50,000 units), and insulin (20 μg). In each case, nasal delivery of these agents significantly ($p<0.001$) reduced susceptibility to SD in neocortex plus hippocampus. Resistance against SD was always greater in hippocampus compared to neocortex (n=4, controls; n=3, acutely after IGF-1; n=6, one day after IGF-1; n=6, one day after IL-11; n=6, one day after IFN-γ; and n=3, acutely after insulin).

Nasal administration followed by SD threshold evaluation in vivo. Vehicle or human recombinant IGF-1 (150 µg) is administered intranasally. SD threshold is established by injection of nanoliter volumes of 0.5 M KCl into neocortex or hippocampus (−2.0 mm from Bregma and 1.5 mm lateral from midline at either 750 µm or 2,800 µm into brain, respectively) using a thin-walled glass pipette and Picospritzer. Once a threshold is established, it is confirmed two more times, with an exemplary record from a vehicle-sham animal shown below. The injection volume is measured by injecting, with the same pressure and duration, the amount of 0.5M KCl that led to the first SD, into a glass well filled with light machine oil (a liquid of appropriate density to maintain a sphere of the injected solution that does not sink). The diameter of the injected sphere is then measured using a compound microscope and used to calculate the injected volume, then moles of potassium. Recordings are made at −6.0 mm from Bregma and 4.5 mm lateral to the midline at either 750 µm or 4,500 µm in depth for neocortex and hippocampus, respectively.

Example 9

Experiments using hippocampal slice cultures demonstrated that phasic IGF-1 markedly protected against SD and this effect was related to reduced oxidative stress.

Spreading depression (SD), the likely cause of migraine aura and perhaps migraine, is triggered by widespread and unfettered neuronal hyperexcitability. Migraine and the initiating hyperexcitability of seizure, which involve oxidative stress (OS), are likely interrelated. Environmental enrichment (EE) decreases seizure and can reduce migraine. EE's well-characterized neuroprotective effect involves insulin-like growth factor-1 (IGF-1). Accordingly, the inventors asked if IGF-1 could mitigate the hyperexcitability that initiates SD using rat hippocampal slice cultures. The inventors demonstrate that IGF-1 significantly decreased SD susceptibility and related OS. The inventors mimicked OS of SD and observed that IGF-1 abolished hyperexcitability from OS. Application of an antioxidant significantly decreased SD susceptibility and co-administration of an antioxidant with IGF-1 produced no additive effect, whereas an oxidizer significantly increased SD, and this effect was abrogated by IGF-1. Moreover, IGF-1 significantly decreased baseline OS, despite seemingly paradoxically increasing CA3 bursting. These results suggest that IGF-1 increased endogenous antioxidants to levels sufficient to buffer against the OS of SD. Insulin similarly mitigated SD susceptibility, but required a far greater dose. Since brain IGF-1 increases with EE, and, like insulin, independently functions as an EE mimetic, the inventors suggest that EE mimetics are a novel source of therapeutics for SD, and by extension, migraine.

Figures 8A, 8B, 8C, 8D, 8E, 8F:
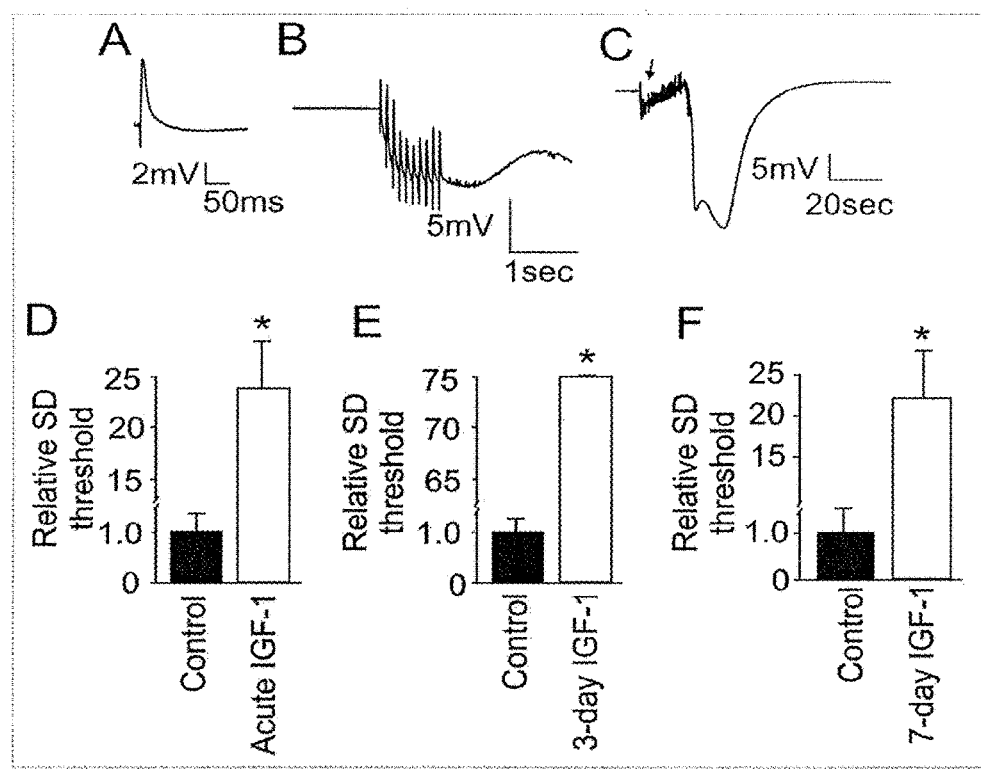
FIGS. 8a-8f IGF-1 reduced spreading depression susceptibility in hippocampal slice cultures.

IGF-1 (and insulin) significantly increased SD threshold. Hippocampal slices were exposed to IGF-1 either acutely (i.e., 15-30 min), for 3 days, or for 7 days prior to assessing the SD threshold. The 7-day IGF-1 exposure was performed phasically to better mimic anticipated effects of EE [i.e., exercise-rest intervals (Will et al., 2004; Kraig et al., 2010)], where slices were exposed to IGF-1-supplemented media in the day and returned to regular media at night. Acute, 3-day, and 7-day exposure to IGF-1 all significantly increased SD threshold compared to control by 24, 75, and 22-fold (FIG. 8). Furthermore, 3-day exposure to insulin [(400 µg/mL); but not lower insulin doses, i.e., 6, 12, and 100 µg/mL (n=3-9/group)] resulted in a significantly (p=0.03) higher SD threshold versus control [i.e., 22.60±9.60 (n=8) and 1.00±0.20 (n=9), respectively]. However, the insulin dose needed for this protective effect was 15 500-fold higher than IGF-1 (i.e., 70 µM versus 4.5 or 10 nM), suggesting that IGF-1 has greater therapeutic utility against SD. Accordingly, the inventors focused our subsequent work on IGF-1.

IGF-1 significantly reduced OS from SD Since SD may increase OS (Viggiano et al. 2011), OS can enhance brain excitability (Muller et al. 1993; Gulati et al. 2005; Waldbaum and Patel 2010), and IGF-1 is involved in antioxidant signaling, the inventors next tested whether IGF-1 treatment altered SD-induced OS. Results show that acute, 3-day, and 7-day treatment with IGF-1 significantly reduced OS from SD (FIG. 9). Seven-day exposure was again phasic, as described for SD threshold studies above. While acute treatment with IGF-1 led to a 20% decrease in OS from SD, 3-day exposure to IGF-1 afforded an even greater level of protection, with a 30% decrease in OS from SD, and 7 days offered a 73% decrease in OS from SD.

Figures 10A, 10B, 10C:
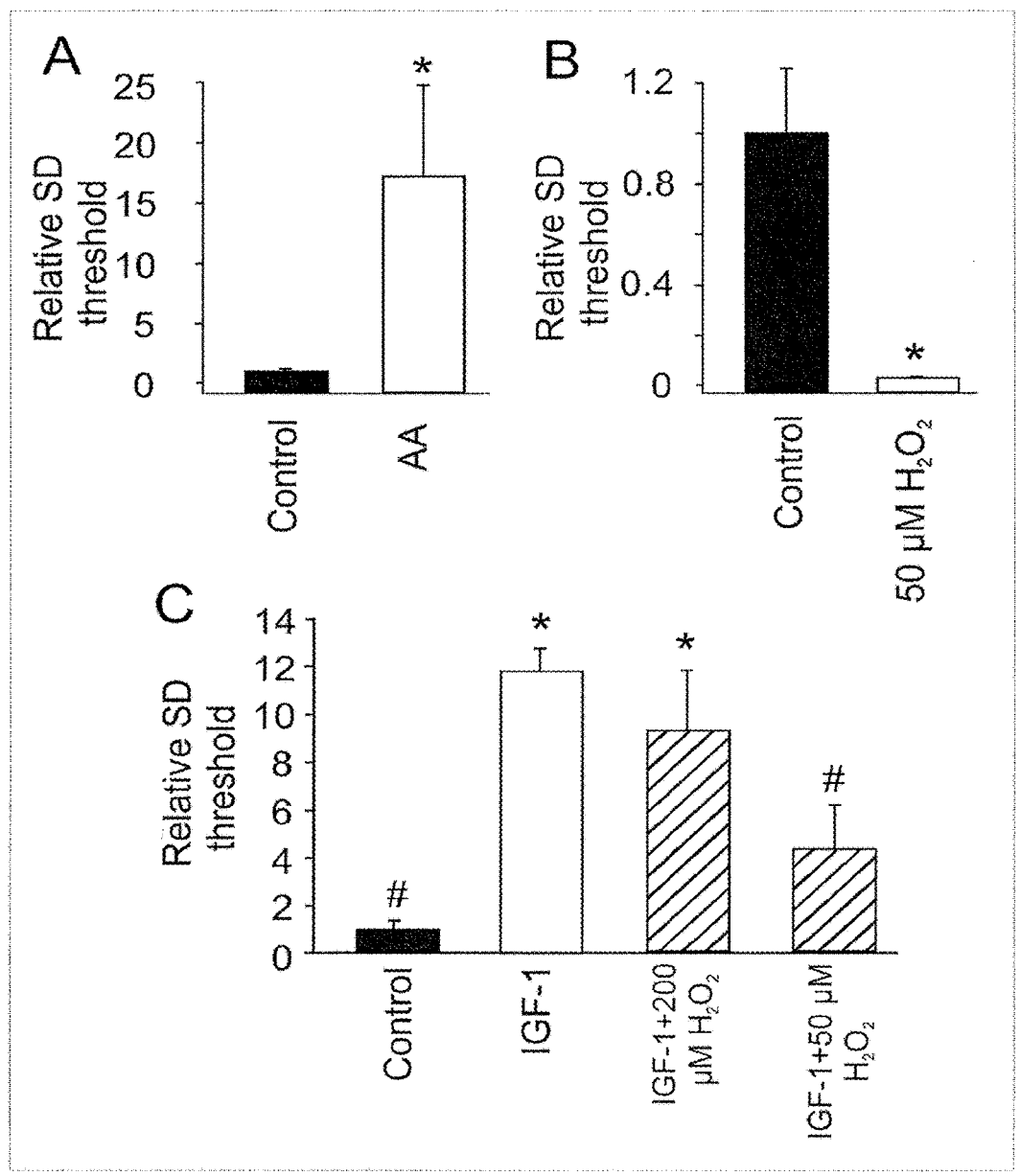
FIGS. 10a-10c The exemplary antioxidant ascorbate reduced, whereas the oxidizer hydrogen peroxide increased, spreading depression susceptibility, with the latter effect abrogated by IGF-1.
Figures 14A, 14B, 14C:
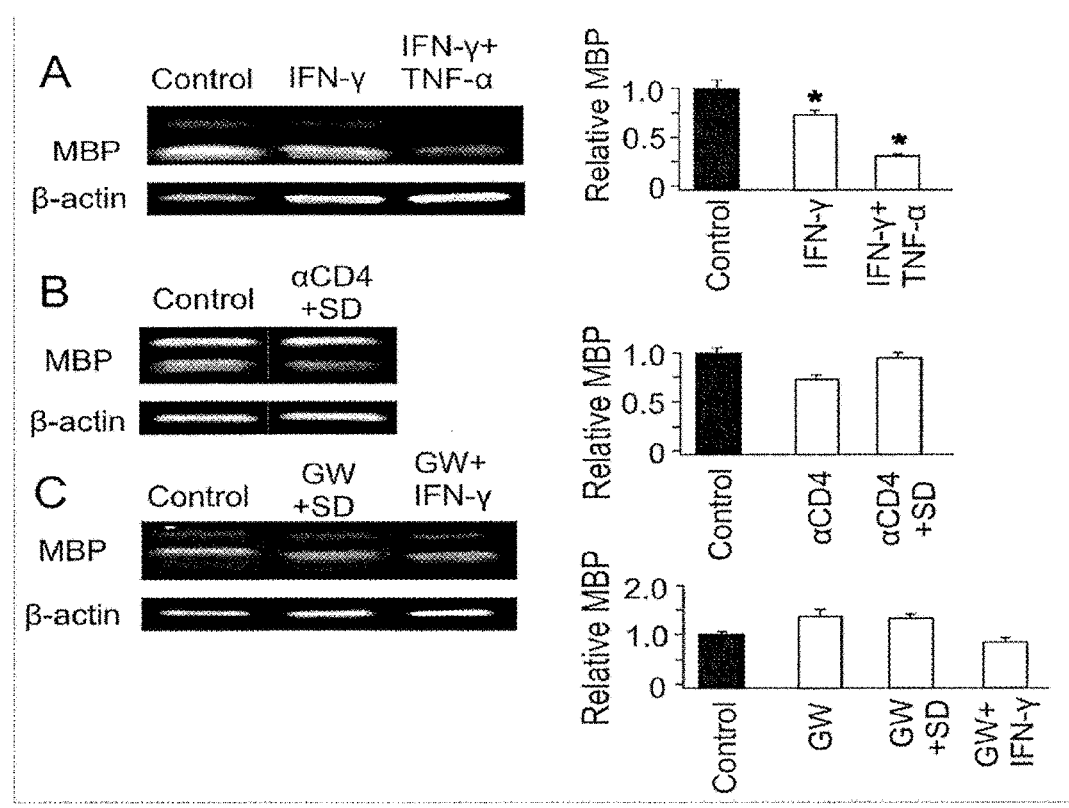
FIGS. 14A-14C. Reduced myelin basic protein (MBP) from SD depends on IFN-γ/T-cell activation and sphingomylinase.

SD susceptibility is modulated by OS. Slices were exposed to either ascorbic acid or hydrogen peroxide and SD threshold was assessed. Ascorbate (2 mM) significantly increased the SD threshold, while hydrogen peroxide (50 µM) significantly decreased the SD threshold (FIG. 14). Co-exposure to IGF-1 and a higher dose of hydrogen peroxide (200 µM) led to a significant decrease in the SD threshold when compared with IGF-1 alone. However, 50 µM hydrogen peroxide co-exposed with IGF-1 was an insufficient oxidant stress to overwhelm the protective effect of IGF-1 on SD susceptibility (FIG. 10). Finally, coincubation of slice cultures with ascorbate and IGF-1 (n=8) did not significantly raise the threshold for SD versus IGF-1 alone (n=7; p=0.28 with relative SD threshold levels of 7.39±6.16 and 1.00±0.31, respectively).

Figures 11A, 11B, 11C, 11D, 11E, 11F, 11G:
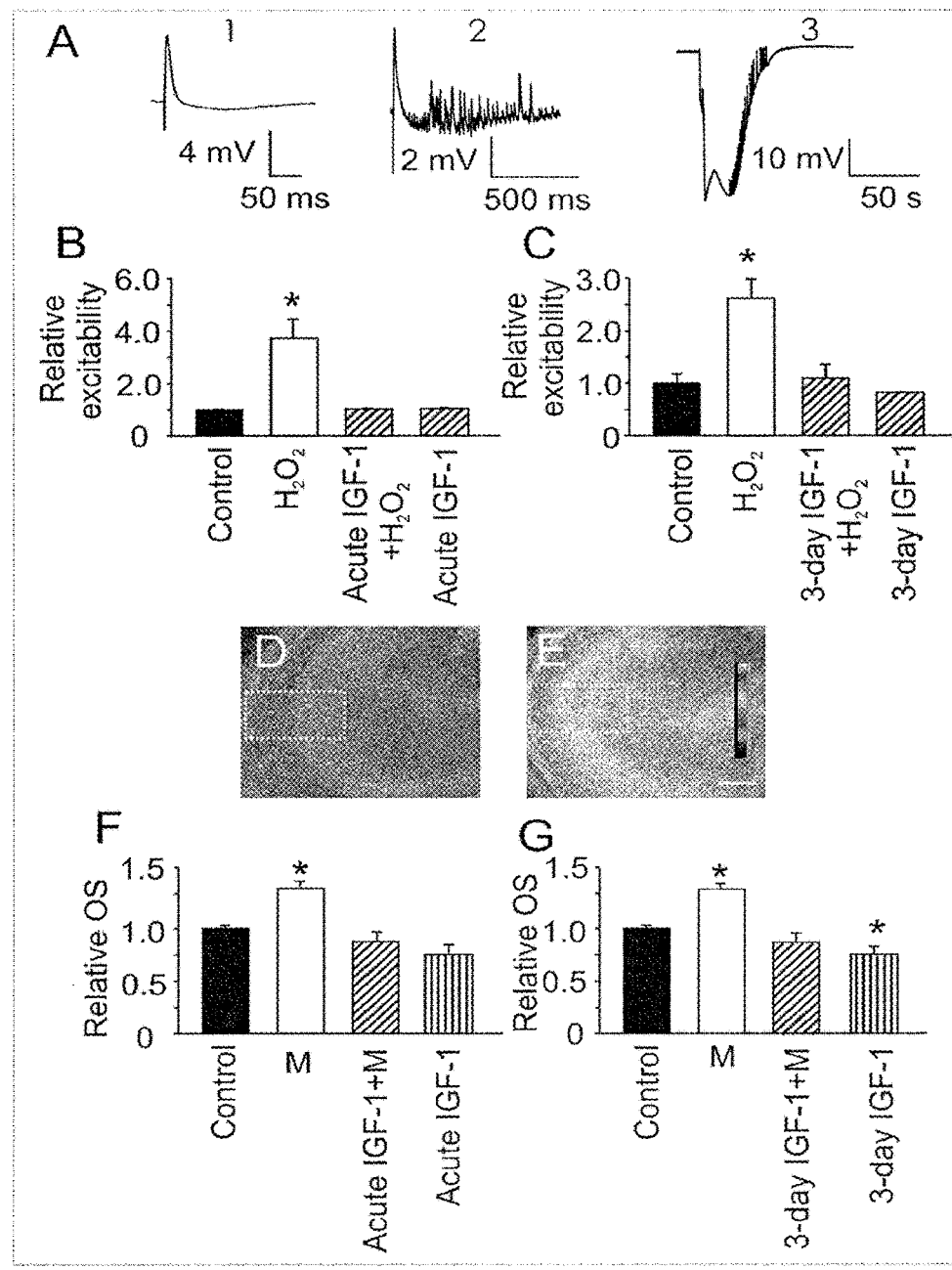
FIGS. 11a-11g IGF-1 decreased CA3 oxidative stress (OS) and its related hyperexcitability.
Figures 12A, 12B, 12C, 12D, 12E:
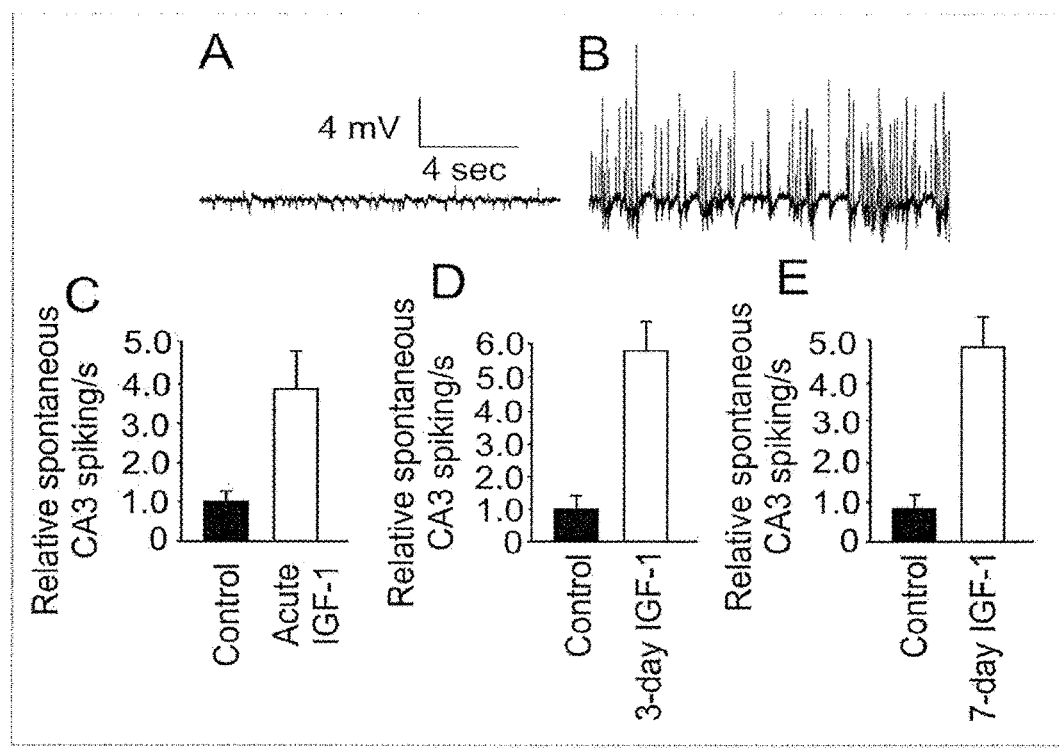
FIGS. 12a-12e IGF-1 increased spontaneous neuronal spiking activity.

IGF-1 eliminated effects of SD-mimetics on excitability and OS. The inventors further assessed the ability of IGF-1 to reduce slice culture excitability by decreasing OS. First, the inventors mimicked OS from SD by application of hydrogen peroxide. This exogenously induced OS significantly increased evoked slice hyperexcitability (FIG. 11), like that seen from SD (Mitchell et al. 2010a). Both 3-day and acute exposure to IGF-1 abrogated this hydrogen peroxide-induced hyperexcitability. Second, the inventors additionally mimicked OS from SD by slice exposure to menadione (FIG. 11). As expected, this treatment triggered a significant increase in slice OS, an effect that was abrogated by acute and 3-day exposure to IGF-1. In fact, 3-day exposure to IGF-1 alone could significantly reduce baseline OS from control levels. Furthermore, 7-day exposure to IGF-1 also significantly reduced baseline OS levels by 26% when compared with controls (p=0.001; n=11 and 9 for controls and 7-day IGF-1, respectively). The latter is important because exposure to IGF-1 alone, which led to the significant reductions in baseline OS (FIG. 11), triggered a significant increase in spontaneous CA3 bursting (FIG. 12).

Example 10

Figure 13:
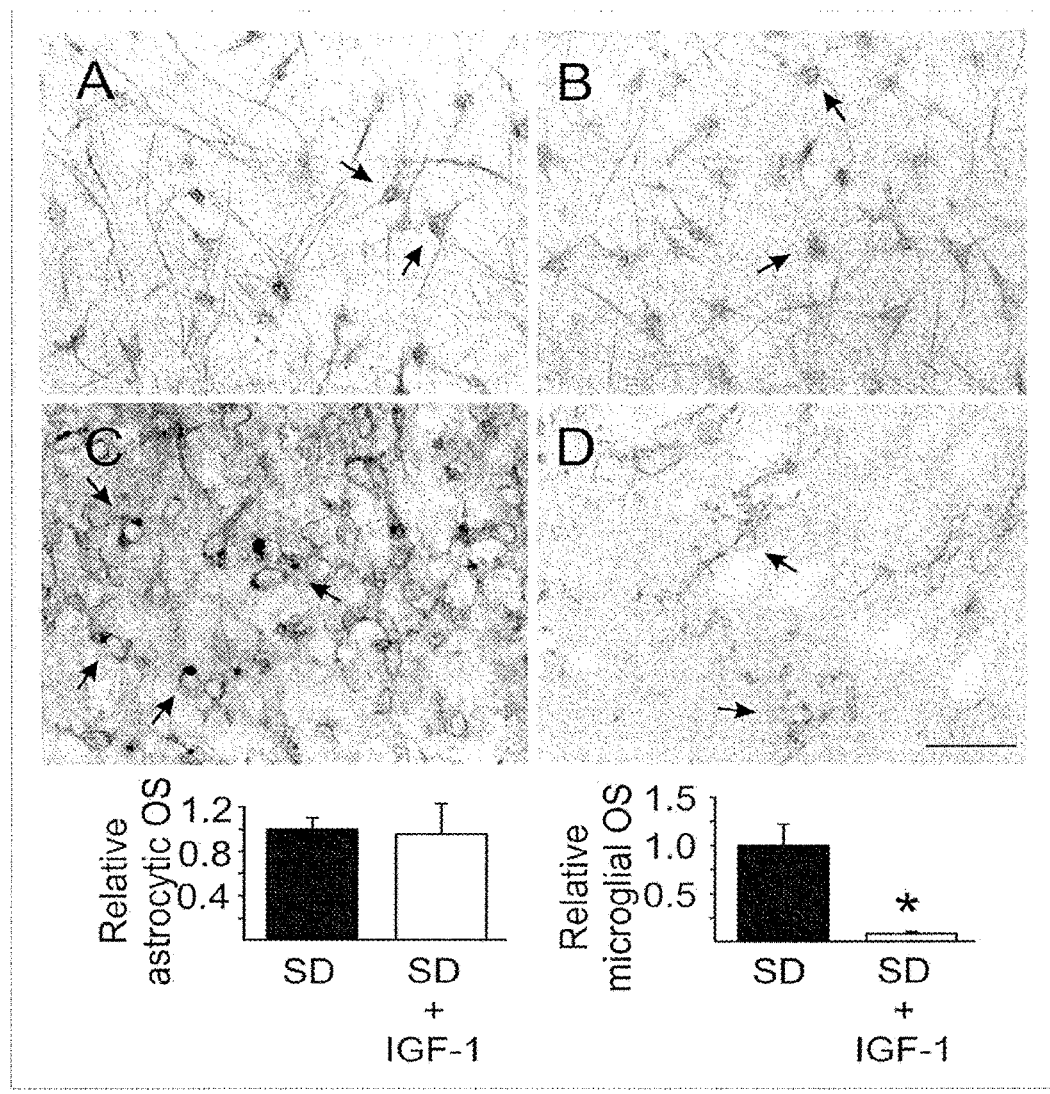
FIG. 13 Oxidative stress from SD preferentially rises in astrocytes and microglia, with the latter effect mitigated by IGF-1. The inventors have recently shown that spreading depression (SD), the most likely cause of migraine aura and perhaps migraine (Lauritzen and Kraig, 2005), occurs with increased oxidative stress (OS) and that OS, in turn, increases SD susceptibility (Grinberg et al., 2012). Reactive oxygen and nitrogen species that cause OS have both autocrine and paracrine signaling capacities that can affect SD susceptibility by altering excitability (Kishida and Klann, 2007). Accordingly, the inventors looked for the cellular origin of OS from SD. Here the inventors used hippocampal slice cultures (HSC) to probe for cell-specific changes in OS from SD. SD was induced trans-synaptically in rat HSCs using bipolar electrical stimuli at the dentate gyrus (Pusic et al., 2011). Six SDs were induced every 7-9 min over an hr, followed by 24 hr incubation in CellROX™, a fixable fluorogenic probe for measuring OS (Grinberg et al., 2012). HSCs were then fixed in 10% buffered formalin phosphate. Other fixatives (PLP, 4% paraformaldehyde) prevented detection of OS change. Tissue was then labeled for neurons (anti-NeuN), oligodendrocytes (anti-RIP), astrocytes (anti-GFAP), or for microglia (isolectin GS-IB4). Using confocal microscopy, followed by MetaMorph analysis of cell-specific fluorescence intensity, the inventors found that OS from SD significantly increased in astrocytes (p=0.019) and microglia (p=0.003) but not in neurons or oligodendrocytes, when compared to sham controls (n=3-6/group). Since the environmental enrichment mimetic insulin-like growth factor-1 (IGF-1) mitigates tissue OS from SD (Grinberg et al., 2012), the inventors next looked for the cell types responsible for this effect. The inventors applied IGF-1 (100 ng/mL) for three days and observed that the OS from SD seen in microglia was significantly (p=0.018) decreased by IGF-1, but astrocytic OS from SD was unchanged. The finding that astrocytes but not neurons show increased OS from SD provides physiologic evidence that extends recent work indicating astrocytes have a higher oxidative metabolism potential (Lovatt et al., 2007). However, the increased astrocytic OS was surprising given their expected high antioxidant potential (Belanger et al., 2011). Furthermore, SD triggers reactive microgliosis (Caggiano and Kraig, 1996), a change that can be expected to occur with increased OS. The results confirm this, but importantly, show IGF-1 selectively abrogated microglial OS. Since OS promotes SD (Grinberg et al., 2012), this work points to microglia and their associated OS as potential therapeutic targets in novel high-frequency and chronic migraine therapeutics.

Oxidative stress from SD preferentially rises in astrocytes and microglia, with the latter effect mitigated by IGF-1 (FIG. 13). The inventors have recently shown that spreading depression (SD), the most likely cause of migraine aura and perhaps migraine (Lauritzen and Kraig, 2005), occurs with increased oxidative stress (OS) and that OS, in turn, increases SD susceptibility (Grinberg et al., 2012). Reactive oxygen and nitrogen species that cause OS have both autocrine and paracrine signaling capacities that can affect SD susceptibility by altering excitability (Kishida and Klann, 2007). Accordingly, the inventors looked for the cellular origin of OS from SD. Here the inventors used hippocampal slice cultures (HSC) to probe for cell-specific changes in OS from SD. SD was induced trans-synaptically in rat HSCs using bipolar electrical stimuli at the dentate gyrus (Pusic et al., 2011). Six SDs were induced every 7-9 min over an hr, followed by 24 hr incubation in CellROX™, a fixable fluorogenic probe for measuring OS (Grinberg et al., 2012). HSCs were then fixed in 10% buffered formalin phosphate. Other fixatives (PLP, 4% paraformaldehyde) prevented detection of OS change. Tissue was then labeled for neurons (anti-NeuN), oligodendrocytes (anti-RIP), astrocytes (anti-GFAP), or for microglia (isolectin GS-IB4). Using confocal microscopy, followed by MetaMorph analysis of cell-specific fluorescence intensity, the inventors found that OS from SD significantly increased in astrocytes ($p=0.019$) and microglia ($p=0.003$) but not in neurons or oligodendrocytes, when compared to sham controls ($n=3-6$/group).

Since the environmental enrichment mimetic insulin-like growth factor-1 (IGF-1) mitigates tissue OS from SD (Grinberg et al., 2012), the inventors next looked for the cell types responsible for this effect. The inventors applied IGF-1 (100 ng/mL) for three days and observed that the OS from SD seen in microglia was significantly ($p=0.018$) decreased by IGF-1, but astrocytic OS from SD was unchanged. The finding that astrocytes but not neurons show increased OS from SD provides physiologic evidence that extends recent work indicating astrocytes have a higher oxidative metabolism potential (Lovatt et al., 2007). However, the increased astrocytic OS was surprising given their expected high antioxidant potential (Belanger et al., 2011). Furthermore, SD triggers reactive microgliosis (Caggiano and Kraig, 1996), a change that can be expected to occur with increased OS. The results confirm this, but importantly, show IGF-1 selectively abrogated microglial OS. Since OS promotes SD (Grinberg et al., 2012), this work points to microglia and their associated OS as potential therapeutic targets in novel high-frequency and chronic migraine therapeutics.

Example 11

The inventors noted above that IFN-γ has detrimental and beneficial effects on oligodendrocytes (e.g., myelin), contrasting responses that mutually involve oxidative stress (OS). Loss of myelin and impaired remyelination in multiple sclerosis, and its animal model, experimental autoimmune allergic encephalomyelitis, involve increased IFN-γ and OS signaling concomitant with disease. Conversely, if occurring prior to disease onset and allowed adequate time for adaptation, elevated IFN-γ and associated OS reduce the degree of demyelination otherwise seen in animal models of multiple sclerosis. While the mechanisms for IFN-γ/OS effects on myelin are incompletely defined, recent evidence suggests involvement of neural activity driven anti-oxidant production.

Environmental enrichment [(EE) i.e., volitionally increased intellectual, social, and physical activity] occurs with enhanced learning and memory from phasically increased neural activity and lessened subsequent injury from a wide array of neurodegenerative disorders including demyelinating diseases. In addition, EE increased T cell trafficking in the brain, expression of IFN-γ, production of myelin, and reduced OS. Importantly, enhanced neuronal activity leads to elevated production of anti-oxidants, including glutathione. Furthermore, glutathione inhibits demyelination by blocking sphingomyelinase, and antioxidants stimulate expression of genes associated with myelination.

As noted above, the inventors probed for further evidence of these potential IFN-γ/OS-antioxidant interactions on brain myelin using mature hippocampal slice cultures, since T cells are present and the tissue shows a rise in IFN-γ after SD. SD is a benign perturbation of brain that is thought to be the most likely cause of migraine aura, and perhaps migraine. When recurrent, SD may also play a role in the conversion of episodic to high frequency and chronic migraine. Furthermore, SD increases OS and experimental demyelination increases susceptibility to SD.

Latest results confirm that when IFN-γ is pulsed onto hippocampal slice cultures OS is reduced, SD susceptibility is reduced, and importantly MBP rises above baseline, effects that appear to be due to increased anti-oxidant production, including glutathione. Reduced myelin basic protein (MBP) from SD depends on IFN-γ/T-cell activation and sphingomylinase (FIG. 18). In contrast, physiological and transient elevation of IFN-γ triggers completely opposite effects (FIG. 19).

Figures 15A, 15B, 15C:
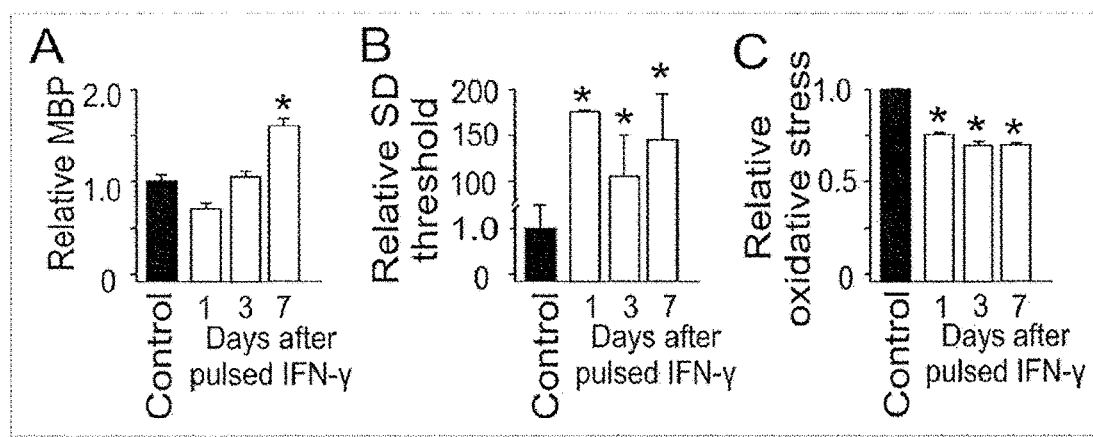
FIGS. 15A-15C. Physiological and transient elevation [i.e., phasic (see FIG. 1)] of IFN-γ triggers completely opposite effects. Transient (i.e., 500 U/mL×12 hours; all groups n≥5) exposure of hippocampal slice cultures was nutritive when assessed seven days later.
Figures 16A, 16B, 16C, 16D, 16E, 16F:
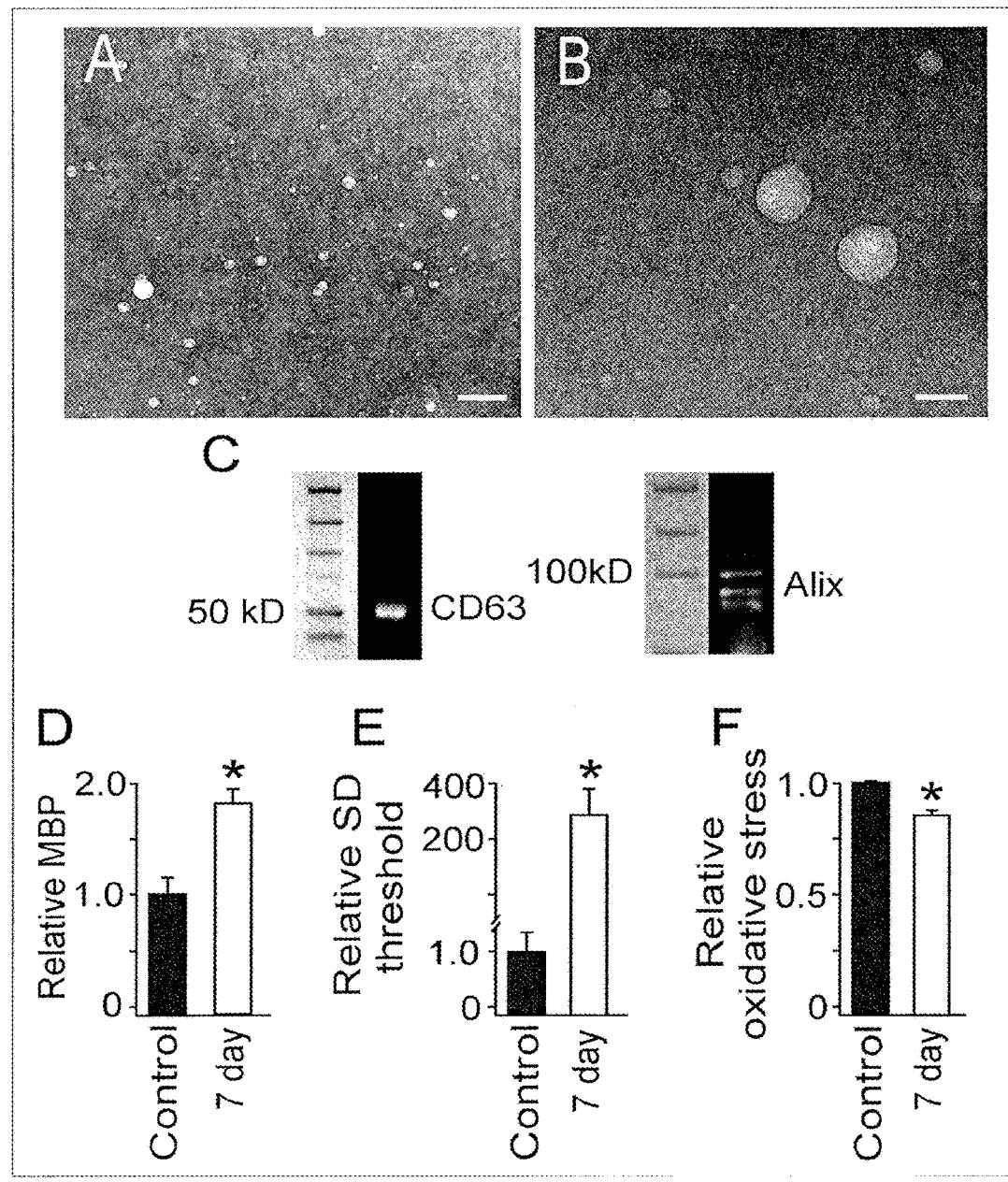
FIGS. 16A-16F. IFN-γ, when pulsed onto slice cultures for 12 hours triggers the release of nutritive exosomes that mimic the effect of pulsed exposure to IFN-γ. Slice cultures were exposed to IFN-γ (500 U/mL×12 hours) and three days later exosomes were harvested from their surrounding incubation media. The latter were then applied to naïve slice cultures and measurements made seven days later. All group sizes were ≥5; all significance measurements p≤0.001. Electron micrographs show exosomes at low (FIG. 16A) and high (FIG. 16B) power; cal bars, 200 and 100 nm, respectively.
Figures 17A, 17B:
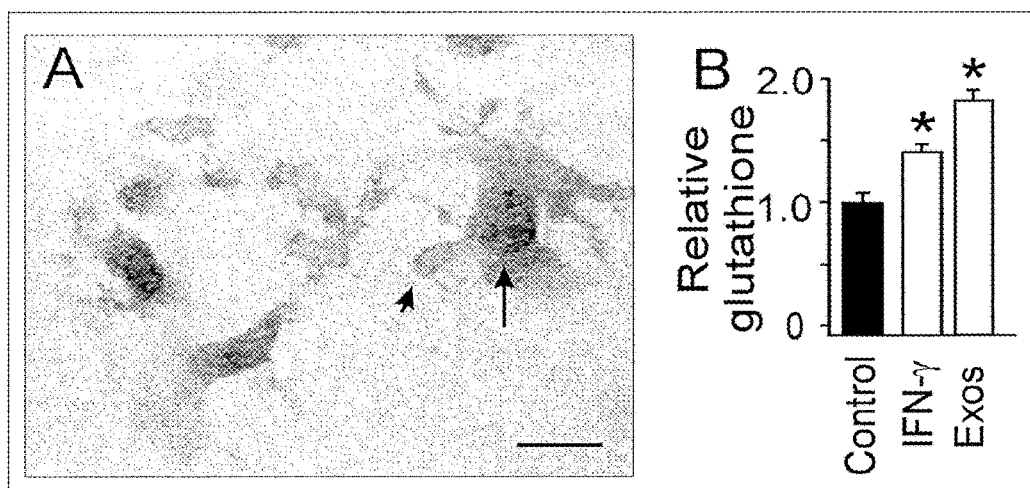
FIGS. 17A-17B. Detection of an IFN-γ-induced rise in slice culture glutathione using Thiol Tracker™, a fluorescent indicator of glutathione.

Since stimulated immune cells release exosomes that are capable of reducing OS in recipient cells, the inventors next tested whether IFN-γ stimulated slice cultures (and possibly their microglia) to release exosomes that mimicked the effects of IFN-γ. The inventor's results confirm this hypothesis (FIGS. 15-17). IFN-γ, when pulsed onto slice cultures for 12 hours triggers the release of nutritive exosomes that mimic the effect of pulsed exposure to IFN-γ (16, 17). Since pulsed-exposure to IFN-γ reduces OS and glutathione is a naturally occurring inhibitor of neutral sphingomyelinase, the inventors probed for an IFN-γ-induced rise in slice culture glutathione using Thiol Tracker™, a fluorescent indicator of glutathione (FIG. 17).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,650,810
U.S. Pat. No. 4,914,125
U.S. Pat. No. 4,994,483
U.S. Pat. No. 5,021,428
U.S. Pat. No. 5,200,413
U.S. Pat. No. 5,242,949

U.S. Pat. No. 5,248,684
U.S. Pat. No. 5,273,759
U.S. Pat. No. 5,317,103
U.S. Pat. No. 5,364,863
U.S. Pat. No. 5,399,363
U.S. Pat. No. 5,399,574
U.S. Pat. No. 5,434,154
U.S. Pat. No. 5,441,969
U.S. Pat. No. 5,464,864
U.S. Pat. No. 5,466,468
U.S. Pat. No. 5,466,699
U.S. Pat. No. 5,468,768
U.S. Pat. No. 5,491,148
U.S. Pat. No. 5,494,910
U.S. Pat. No. 5,543,158
U.S. Pat. No. 5,580,579
U.S. Pat. No. 5,629,001
U.S. Pat. No. 5,641,515
U.S. Pat. No. 5,725,871
U.S. Pat. No. 5,756,353
U.S. Pat. No. 5,780,045
U.S. Pat. No. 5,792,451
U.S. Pat. No. 5,804,212
U.S. Pat. No. 6,613,308
U.S. Pat. No. 6,753,514
Akpan et al., *J. Neurosci.*, 31:8894-8904, 2011.
Aurora *Neurology*, 72(suppl):S3-S13, 2009.
Beattie et al., *Science*, 295:2282-2285, 2002.
Belanger et al., *Cell Metab* 14(6):724-738, 2011.
Benedict et al., *Psychoneuroendocrinology*, 29(10):1326-34, 2004.
Berg, In: *Random Walks in Biology*, Princeton Univ. Press, N Y, 1993.
Born et al., *Nat. Neurosci.*, 5:514-516, 2002.
Brazier, *Electroencephalogr. Clin. Neurophysiol.*, 24:55-67, 1963.
Bures et al., In: *The mechanisms and applications of Leão's spreading depression of electroencephalographic activity*, Prague, Academia, 1974.
Cabrera and Milton, *Chaos.*, 14(3):691-698, 2004.
Caggiano et al., *J. Comp. Neurol.*, 376:447-462, 1996.
Carro et al., *J. Neuroscience*, 20:2926-2933, 2000.
Chen et al., *Free Radic. Biol. Med.*, 46:1204-1210, 2009.
Chen et al., *J. Neurosci. Methods*, 171:239-247, 2008.
Clark et al., *J. Neurosci.*, 20:8853-8860, 2000.
Correa et al., *Glia*, 59:785-799, 2011.
Costa-Mattioli et al., *Cell*, 129:195-206, 2007.
Costa-Mattioli et al., *Nature*, 436:1166-1173, 2005.
Costa-Mattioli et al., *Neuron*, 61:10-26, 2009.
Darabaneanu et al., *Int. J. Sports Med.*, 32:455-460, 2011.
De Rosa et al., *Proc. Natl. Acad. Sci. USA*, 102:3811-3816, 2005.
Empl et al., *Cephalalgia*, 19:713-717, 1999.
Engelhardt and Ransohoff, *Trends Immunol.*, 26:485-495, 2005.
Gkogkas et al., *J. Biol. Chem.*, 285:31913-31917, 2010.
Gobbo and O'Mara, *Behav. Brain Res.*, 152:231-241, 2004.
Goddard et al., *Proc. Natl. Acad. Sci. USA*, 104(16):6828-6833, 2007.
Grinberg and Kraig, *Soc. Neurosci.*, 38: (in press), 2012b.
Grinberg et al., *J. Neurochem.*, 122:221-229, 2012a.
Guedes et al., *Rev. Bras. Biol.*, 56(Su 1 Pt 2):293-301, 1996.
Hallschmid et al., *Regul. Pept.*, 149:79-83, 2008.
Haskew-Layton et al., *Proc. Natl. Acad. Sci. USA*, 107:17385-17390, 2010.
Hulse et al., *J. Neurosci.*, 28:12199-12211, 2008.
Hung et al., *Neuropharmacology*, 58(2):321-329, 2010.
Hwang et al., *Crit. Rev. Ther. Drug Carrier Syst.*, 15(3):243-284, 1998.
Hwang et al., *Neurochem. Int.*, 45:149-156, 2004.
Imitola et al., *Pharmacol. Ther.*, 106:163-177, 2005.
Jogie-Brahim et al., *Endocr. Rev.*, 30:417-437, 2009.
Juurlink et al., *Glia*, 22:371-378, 1998.
Kaneko et al., *Invest. Ophthalmol. Vis. Sci.*, 49(9):4162-4168, 2008.
Kim et al., *Cell* 120(2): 195-208, 2005.
Kishida and Klann, *Antioxid Redox Sign*1225al, 9(2):233-44, 2007.
Kopec et al., *J. Neurosci.*, 26:2000-2009, 2006.
Kraig et al., *Dose Response*, 8:389-413, 2010.
Kriegler, In: *Gene Transfer and Expression*, A Laboratory Manual, W. H. Freeman Co, NY, 1990.
Kruger et al., *Neuroreport*, 7:2733-2736, 1996.
Kunkler and Kraig, *Hippocampus*, 13:835-844, 2003.
Kunkler and Kraig, *J. Cereb. Blood Flow Metab.*, 17(1):26-43, 1997.
Kunkler and Kraig, *J. Neurosci.*, 18:3416-3425, 1998.
Kunkler et al., *J. Cereb. Blood Flow Metab.*, 24:829-839, 2004.
Kunkler et al., *J. Neurosci.*, 25:3952-3961, 2005.
Kunkler et al., *Soc Neurosci*, 32:87.5, 2006.
Kyte and Doolittle, *J. Mol. Biol.*, 157(1):105-132, 1982.
Lauritzen and Kraig, In: *The Headaches*, Olesen et al. (Eds.), 3rd Ed., Lippincott-Raven, Philadelphia, 269-276, 2005.
Lees and Cross, *J. Clin. Invest.*, 117:297-299, 2007.
Li et al., *J. Neurosci.*, 28:1085-1098, 2008.
Lin et al., *Am. J. Pathol.*, 173:1508-1517, 2008.
Liu et al., *J. Neurol. Sci.*, 187:91-97, 2001.
Lovatt et al., *J. Neurosci.*, 27(45):12255-6, 2007.
Mansuy et al., *Cell*, 92:39-49, 1998.
Mathiowitz et al., *Nature*, 386(6623):410-414, 1997.
McGlade-McCulloh et al., *Proc. Natl. Acad. Sci. USA*, 86(3):1093-1097, 1989.
Mendes et al., *Eur. Arch. Psychiatry Clin. Neurosci.*, 259:16-22, 2009.
Merkler et al., *Ann. Neurol.*, 66:355-365, 2009.
Mitchell et al., *J. Neurochem.*, 117:187-196, 2011.
Mitchell et al., *J. Vis. Exp.*, 43:pii 2192, 2010.
Mody et al., *J. Neurophysiol.*, 57(3):869-888, 1987.
Mumby et al., *Learn Mem.*, 9:49-57, 2002.
Murray, In: *Methods in Molecular Biology*, Vol. 7, Humana Press Inc., Clifton, N.J., 1991.
Nimmerjahn et al., *Science*, 308(5726):1314-1318, 2005.
Nishijima et al., *Neuron*, 67:834-846, 2010.
Nunez et al., *J. Neurophysiol.*, 89:3008-3017, 2003.
Otmakhov et al., *J. Neurophysiol.*, 91:1955-1962, 2004a.
Otmakhov et al., *J. Neurosci.*, 24:9324-9331, 2004b.
Papadia et al., *Nat. Neurosci.*, 11:476-487, 2008.
PCT Appln. PCT/US2009/046438
Popko et al., *Mol. Neurobiol.*, 14:19-35, 1997.
Pusic and Kraig, *Soc. Neurosci*, 36: Prog #346.2, 2010.
Pusic et al., *J. Vis. Exp.*, 52:2910, 2011.
Ramirez et al., *Am. J. Pathol.*, 176:881-892, 2010.
Rampon et al., *Nat. Neurosci.*, 3:238-244, 2000.
Ramsey et al., *J. Neurophysiol.*, 94:247-254, 2005.
Remington's Pharmaceutical Sciences, 15th Ed., 1035-1038 and 1570-1580, 1990.
Remington's Pharmaceutical Sciences, 18th Ed. Mack Printing Company, 1289-1329, 1990.
Ren et al., *Proc. Natl. Acad. Sci. USA*, 108:1433-1438, 2011.
Reynolds, *Am. Nat.*, 175(5):607-613, 2010b.
Reynolds, *J. R. Soc. Interface*, 7(53):1753-1758, 2010a.
Rohl et al., *Glia*, 56:1114-1126, 2008.

Romera et al., *J. Neurosci.*, 24:1350-1357, 2004.
Ruby et al., *Proc. Natl. Acad. Sci. USA*, 105:15593-15598, 2008.
Rutten et al., *J. Neurosci. Methods*, 171:72-77, 2008.
Selmeczi et al., *Biophys. J.*, 89(2):912-931, 2005.
Selmeczi et al., In: *The European Physical Journal Special Topics*, 157(1):1-15, Springer Berlin/Heidelberg, 2008.
Shao and Dudek, *J. Physiology*, 587:5907-5923, 2009.
Shin et al., *Neurochem. Int.*, 52:1134-1147, 2008.
Silberstein and Olesen, In: *The Headaches*, 3rd Ed., Olesen et al. (Eds.), 613-617, Philadelphia, Lippincott-Raven, 2005.
Somjen, *Physiol. Rev.*, 81:1065-1096, 2001.
Steinmetz and Turrigiano, *J. Neurosci.*, 30(44):14685-14690, 2010.
Stellwagen and Malenka, *Nature*, 440(7087):1054-1059, 2006.
Stellwagen et al., *J. Neurosci.*, 25:3219-3228, 2005.
Stockhorst et al., *Physiol. Behav.*, 83:47-54, 2004.
Takagi et al., *PLoS One* 3, e2648, 2008.
Takenaga et al., *J. Control Release*, 52(1-2):81-87, 1998.
Tay et al., *Nature*, 466:267-271, 2010.
Thorne et al., *Neuroscience*, 127:481-496, 2004.
Thuret et al., *Hippocampus*, 19:658-669, 2009.
Viswanathan et al., *Nature*, 401:911, 1999.
Waldbaum and Patel, *Epilepsy Res.*, 88(1):23-45, 2010.
Waldbaum and Dudek, *Epilepsia*, 50:904-916, 2009.
Young et al., *Nat. Med.*, 5:448-453, 1999.
Ziv et al., *Nat. Neurosci.*, 9:268-275, 2006.

---

What is claimed is:

1. A method for treating a patient subject to seizures comprising administering to the patient an effective amount of a composition comprising insulin growth factor-1 (IGF-1), wherein treating excludes administering a cytokine to the patient.

2. The method of claim 1, wherein the composition is administered intranasally.

3. The method of claim 1, wherein the composition is administered multiple times.

4. The method of claim 1, wherein the composition is administered on multiple days.

5. The method of claim 1, wherein the composition is administered on multiple consecutive days.

* * * * *

UNITED STATES PATENT AND TRADEMARK OFFICE
CERTIFICATE OF CORRECTION

PATENT NO. : 10,391,150 B2  
APPLICATION NO. : 15/791802  
DATED : August 27, 2019  
INVENTOR(S) : Richard Kraig et al.

Page 1 of 1

It is certified that error appears in the above-identified patent and that said Letters Patent is hereby corrected as shown below:

On the Title Page

In Item [73] Assignee, "Universit" should read --University--.

Signed and Sealed this  
Twenty-eighth Day of January, 2020

Andrei Iancu  
*Director of the United States Patent and Trademark Office*

SEQUENCE LISTING

```
<160> NUMBER OF SEQ ID NOS: 4

<210> SEQ ID NO 1
<211> LENGTH: 166
<212> TYPE: PRT
<213> ORGANISM: Homo sapiens

<400> SEQUENCE: 1

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 2
<211> LENGTH: 199
<212> TYPE: PRT
<213> ORGANISM: Homo sapiens

<400> SEQUENCE: 2

Met Asn Cys Val Cys Arg Leu Val Leu Val Val Leu Ser Leu Trp Pro
1               5                   10                  15

Asp Thr Ala Val Ala Pro Gly Pro Pro Gly Pro Pro Arg Val Ser
            20                  25                  30

Pro Asp Pro Arg Ala Glu Leu Asp Ser Thr Val Leu Leu Thr Arg Ser
        35                  40                  45
```

```
Leu Leu Ala Asp Thr Arg Gln Leu Ala Ala Gln Leu Arg Asp Lys Phe
     50                  55                  60

Pro Ala Asp Gly Asp His Asn Leu Asp Ser Leu Pro Thr Leu Ala Met
 65                  70                  75                  80

Ser Ala Gly Ala Leu Gly Ala Leu Gln Leu Pro Gly Val Leu Thr Arg
                 85                  90                  95

Leu Arg Ala Asp Leu Leu Ser Tyr Leu Arg His Val Gln Trp Leu Arg
                100                 105                 110

Arg Ala Gly Gly Ser Ser Leu Lys Thr Leu Glu Pro Glu Leu Gly Thr
            115                 120                 125

Leu Gln Ala Arg Leu Asp Arg Leu Leu Arg Arg Leu Gln Leu Leu Met
130                 135                 140

Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
            180                 185                 190

Leu Leu Leu Lys Thr Arg Leu
            195

<210> SEQ ID NO 3
<211> LENGTH: 119
<212> TYPE: PRT
<213> ORGANISM: Homo sapiens

<400> SEQUENCE: 3

Met Ala Leu Cys Leu Leu Thr Phe Thr Ser Ala Thr Ala Gly Pro
 1               5                  10                  15

Glu Thr Leu Cys Gly Ala Glu Leu Val Asp Ala Leu Gln Phe Val Cys
                 20                  25                  30

Gly Asp Arg Gly Phe Tyr Phe Asn Lys Pro Thr Gly Tyr Gly Ser Ser
             35                  40                  45

Ser Arg Arg Ala Pro Gln Thr Gly Ile Val Asp Glu Cys Cys Phe Arg
 50                  55                  60

Ser Cys Asp Leu Arg Arg Leu Glu Met Tyr Cys Ala Pro Leu Lys Pro
 65                  70                  75                  80

Ala Lys Ser Ala Arg Ser Val Arg Ala Gln Arg His Thr Asp Met Pro
                 85                  90                  95

Lys Thr Gln Lys Glu Val His Leu Lys Asn Ala Ser Arg Gly Ser Ala
                100                 105                 110

Gly Asn Lys Asn Tyr Arg Met
            115

<210> SEQ ID NO 4
<211> LENGTH: 110
<212> TYPE: PRT
<213> ORGANISM: Homo sapiens

<400> SEQUENCE: 4

Met Ala Leu Trp Met Arg Leu Leu Pro Leu Leu Ala Leu Leu Ala Leu
 1               5                  10                  15

Trp Gly Pro Asp Pro Ala Ala Ala Phe Val Asn Gln His Leu Cys Gly
                 20                  25                  30

Ser His Leu Val Glu Ala Leu Tyr Leu Val Cys Gly Glu Arg Gly Phe
             35                  40                  45
```

-continued

```
Phe Tyr Thr Pro Lys Thr Arg Arg Glu Ala Glu Asp Leu Gln Val Gly
    50                  55                  60

Gln Val Glu Leu Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```